US011618773B2

(12) United States Patent
Hecker et al.

(10) Patent No.: US 11,618,773 B2
(45) Date of Patent: Apr. 4, 2023

(54) NFAT BINDING POLYNUCLEOTIDES

(71) Applicant: Universität Heidelberg, Heidelberg (DE)

(72) Inventors: Markus Hecker, Heidelberg (DE); Andreas Wagner, Heidelberg (DE); Andreas Jungmann, Neckargemünd (DE); Oliver Müller, Heikendorf (DE); Anca Remes, Kiel (DE); Hugo Katus, Heidelberg (DE)

(73) Assignee: Universität Heidelberg, Heidelberg (DE)

(*) Notice: Subject to any disclaimer, the term of this patent is extended or adjusted under 35 U.S.C. 154(b) by 0 days.

(21) Appl. No.: 16/962,427

(22) PCT Filed: Jan. 14, 2019

(86) PCT No.: PCT/EP2019/050833
§ 371 (c)(1),
(2) Date: Jul. 15, 2020

(87) PCT Pub. No.: WO2019/138114
PCT Pub. Date: Jul. 18, 2019

(65) Prior Publication Data
US 2021/0070820 A1 Mar. 11, 2021

(30) Foreign Application Priority Data
Jan. 15, 2018 (EP) .................... 18151695

(51) Int. Cl.
| C07K 14/47 | (2006.01) |
| A61K 31/713 | (2006.01) |
| C07H 21/00 | (2006.01) |
| C12N 15/113 | (2010.01) |
| A61K 38/00 | (2006.01) |

(52) U.S. Cl.
CPC ........ *C07K 14/4702* (2013.01); *A61K 31/713* (2013.01); *C07H 21/00* (2013.01); *C12N 15/113* (2013.01); *A61K 38/00* (2013.01); *C12N 2310/13* (2013.01)

(58) Field of Classification Search
CPC .............. C12N 15/113; C12N 2310/11; C12N 2310/14; C12N 2310/321; C12N 2310/344; C12N 2310/347; C12N 3521/533
USPC ...................... 435/6.1, 91.1, 91.31, 455, 458; 514/44 A, 44 R; 536/23.1, 24.5
See application file for complete search history.

(56) References Cited

U.S. PATENT DOCUMENTS

| 2011/0178283 A1* | 7/2011 | Rigoutsos | G16B 30/00 536/24.5 |
| 2020/0054673 A1* | 2/2020 | Ports | G01N 33/57496 |

FOREIGN PATENT DOCUMENTS

WO 9218522 A1 10/1992

OTHER PUBLICATIONS

Nakamura et al. (Int Arch Allergy Immunol. 2011;155(2):129-40) (Year: 2011).*
International Preliminary Report on Patentability; The International Bureau of WIPO; International Application No. PCT/EP2019/050833; dated Jul. 21, 2020; 7 pages.
Meriem Bourajjaj et al.; NFATc2 is a Necessary Mediator of Calcineurin-Dependent Cardiac Hypertrophy and Heart Failure; The Journal of Biological Chemistry; Aug. 8, 2008; 10 pages; vol. 283, No. 32.
W. Michael Flanagan; Nuclear Association of a T-Cell Transcription Factor Blocked by FK-506 and Cyclosporin A; Letters to Nature; Aug. 29, 1991; 5 pages; vol. 352.
Lorena Garcia-Menendez et al.; Substrain Specific Response to Cardiac Pressure Overload in C57BL/6 Mice; American Journal of Physiology Heart and Circulatory Physiology; May 24, 2013; 14 pages; vol. 305, No. 3.
Lee R. Goldberg; In the Clinic Heart Failure; Annals of Internal Medicine; Jun. 1, 2010; 16 pages.
RD Hannan et al.; Cardiac Hypertrophy: A Matter of Translation; Clinical and Experimental Pharmacology and Physiology; 2003; 11 pages; vol. 30.
Markus Hecker et al.; Decoy Oligodeoxynucleolides to Treat Inflammatory Diseases; RSC Biomolecular Sciences; 2008; 26 pages.
Katsuya Inagaki et al.; Robust Systemic Transduction with AAV9 Vectors in Mice: Efficient Global Cardiac Gene Transfer Superior to That of AAV8; Mol Ther; Jul. 2006; 18 pages; vol. 14, No. 1.
Ellen C. Jensen; Quantitative Analysis of Histological Staining and Fluorescence Using ImageJ; The Anatomical Record; 2013; 4 pages; vol. 296.
Mitsuhito Kuriyama et al.; A Cell-Permeable NFAT Inhibitor Peptide Prevents Pressure-Overload Cardiac Hypertrophy; Chem Biol Drug Des; 2006; 6 pages; vol. 67.
A. Laupacis et al.; Cyclosporin A: A Powerful Immunosuppressant; Therapeutic Review; May 1, 1982; 6 pages; vol. 126.

(Continued)

*Primary Examiner* — Jane J Zara
(74) *Attorney, Agent, or Firm* — Taft Stettinius & Hollister LLP

(57) ABSTRACT

The present invention relates to a polynucleotide comprising a Nuclear factor of activated T-cells (NFAT) binding site sequence and a reverse complement of said NFAT binding site sequence separated by a spacer sequence, to said polynucleotide for use in treating and/or preventing disease, and to viral particles, compositions, and uses related thereto. The present invention further relates to a polynucleotide comprising a Nuclear factor of activated T-cells (NFAT) binding site sequence and a reverse complement of said NFAT binding site sequence for use in treating and/or preventing an NFAT-mediated disease.

15 Claims, 25 Drawing Sheets

Figure 1:
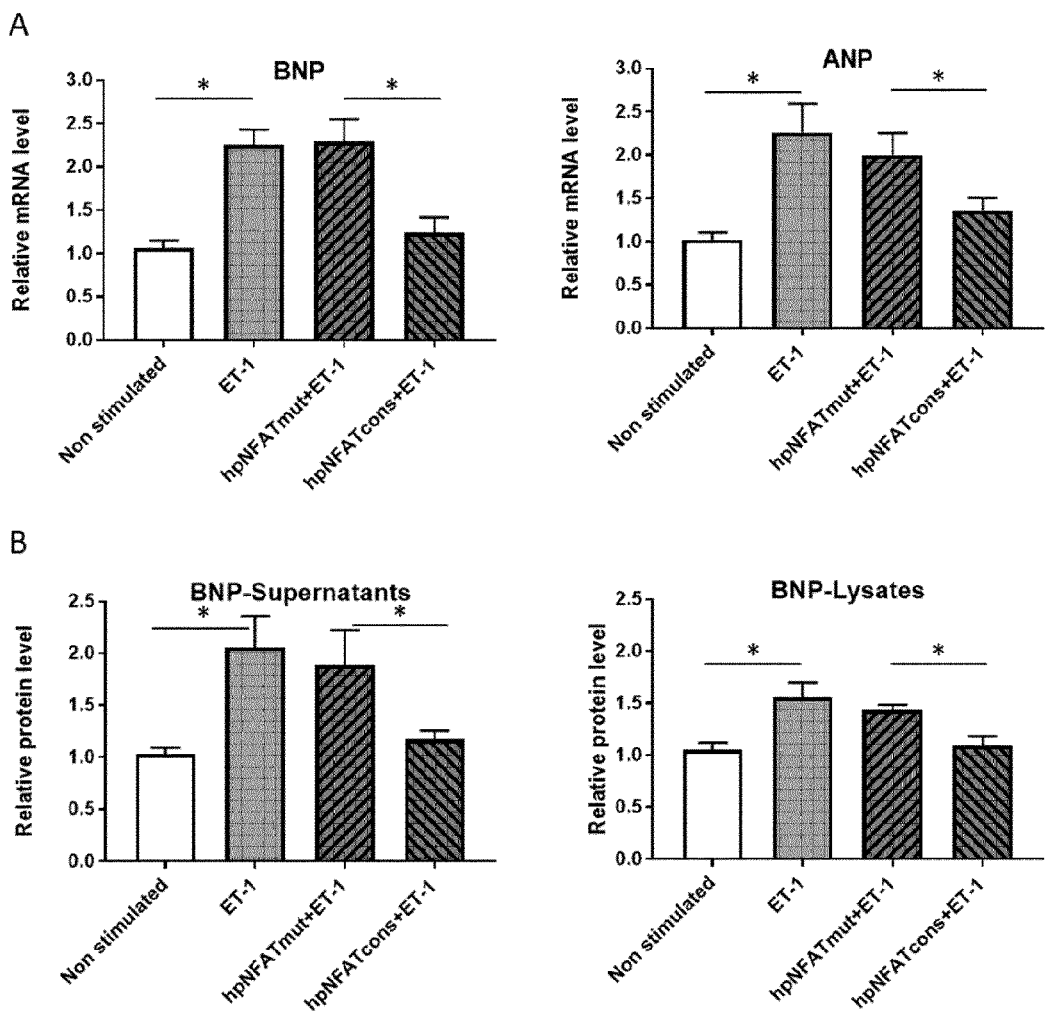

Specification includes a Sequence Listing.

(56) References Cited

OTHER PUBLICATIONS

Lorenz H. Lehmann et al.; Essential Role of Sympathetic Endothelin A Receptors for Adverse Cardiac Remodeling; PNAS; Sep. 16, 2014; 6 pages; vol. 111, No. 37.
Mc Mak et al.; Embryonic Lethality in Mice Lacking the Nuclear Factor of Activated T Cells 5 Protein Due to Impaired Cardiac Development and Function; The HKU Scholars Hub, The University of Hong Kong; PLoS One; 2011; 9 pages; vol. 6, No. 7.
Jeffery D. Molkentin et al.; A Calcineurin-Dependent Transcriptional Pathway for Cardiac Hypertrophy; Cell; Apr. 17, 1998; 14 pages; vol. 93.
Valentina Parra et al.; Calcineurin Signaling in the Heart: The Importance of Time and Place; Journal of Molecular and Cellular Cardiology; 2017; 16 pages; vol. 103.
Michael W. Pfaffl; A New Mathematical Model for Relative Quantification in Real-Time RT-PCR; Nucleic Acids Research; 2001; 6 pages; vol. 29, No. 9.
Anca Remes et al.; Transcription Factor Decoy Oligodeoxynudeotide-Based Prevention of Myocardial Hypertrophy; Institute of Physiology and Pathophysiology; Mar. 31, 2016; 15 pages; vol. 105, No. 1.
A. Remes et al.; V506—NFAT Decoy Oligonudeotide Prevention of Myocardial Hypertrophy; Clin Res Cardiol; Mar. 2016; 1 page; vol. 105, Suppl 1.
Enrico K. Schmidt et al.; SUnSET, A Nonradioactive Method to Monitor Protein Synthesis; Nature Methods; Apr. 2009; 3 pages; vol. 6, No. 4.
K. Varadi et al.; Novel Random Peptide Libraries Displayed on AAV Serotype 9 for Selection of Endothelial Cell-Directed Gene Transfer Vectors; Gene Therapy; 2012; 10 pages; vol. 19.
Sheng Wei et al.; T-Tubule Remodeling During Transition from Hypertrophy to Heart Failure; Integrative Physiology; Circulation Research; Aug. 20, 2010; 12 pages; vol. 107.
Brian M. Wile et al.; Molecular Beacon Enabled Purification of Living Cells by Targeting Cell-Type Specific mRNAs; Nat Protoc.; Feb. 12, 2015; 30 pages; vol. 9, No. 10.
Benjamin J. Wilkins et al.; Calcineurin/NFAT Coupling Participates in Pathological, but not Physiological, Cardiac Hypertrophy; Circulation Research; Jan. 9/23, 2004; 9 pages; vol. 94.
International Search Report; European Patent Office; International Application No. PCT/EP2019/050833; dated Mar. 8, 2019; 5 pages.
Written Opinion of the International Search Authority; European Patent Office; International Application No. PCT/EP2019/050833; dated Mar. 8, 2019; 6 pages.
Yutaka Nakamura et al.; Novel Ribbon-Type Nuclear Factor of Activated T Cells Decoy Oligodeoxynucleotides Preclude Airways Hyperreactivity and Th2 Cytokine Expression in Experimental Asthma; International Archives of Allergy and Immunology; 2011; 12 pages; vol. 155.
T Xiao et al.; Phosphorylation of NFAT3 by CDK3 Induces Cell Transformation and Promotes Tumor Growth in Skin Cancer; Oncogene; 2017; 11 pages; vol. 36.
Markus Hecker et al.; Transcription Factor Decoy Technology: A Therapeutic Update; Elsevier; Biochemical Pharmacology; 2017; 6 pages; vol. 144.

\* cited by examiner

NFAT BINDING POLYNUCLEOTIDES

CROSS-REFERENCE TO RELATED APPLICATIONS

This application is a U.S. National Phase of International PCT Application No. PCT/EP2019/050833 filed Jan. 14, 2019, which claims priority to European Patent Application Serial No. 18151695.6, filed Jan. 15, 2018, the contents of each application are incorporated herein by reference in their entirety.

The present invention relates to a polynucleotide comprising a Nuclear factor of activated T-cells (NFAT) binding site sequence and a reverse complement of said NFAT binding site sequence separated by a spacer sequence, to said polynucleotide for use in treating and/or preventing disease, and to viral particles, compositions, and uses related thereto. The present invention further relates to a polynucleotide comprising a Nuclear factor of activated T-cells (NFAT) binding site sequence and a reverse complement of said NFAT binding site sequence for use in treating and/or preventing an NFAT-mediated disease.

Cardiac remodeling, also referred to as ventricular remodeling, is a process changing size, shape, structure and/or function of the heart. In pathological remodeling, the remodeling process is caused by myocardial infarction or may be caused by increased pressure in the outflow tract or volume in the ventricle, causing pressure overload or volume overload of the heart (Goldberg L R. In the clinic. Heart failure. Ann Intern Med. 2010 June 1; 152(11):ITC61-15). Treatment of pathological cardiac remodeling includes attempts to remove the cause of remodeling, e.g. by adjusting arterial blood pressure in the patient or by correcting malfunctioning cardiac valves. Characteristically, patients suffering from cardiac remodeling are only identified once the process has become symptomatic which is upon transition of heart hypertrophy to insufficiency or even later. As a consequence, treatment typically is symptomatic without allowing for significant retardation or even reversal of the disease. This situation is aggravated by the fact that not adequately treated arterial hypertension or valvular dysfunction (stenosis) frequently lead to maladaptive remodeling of the heart muscle, in which cardiac myocytes are replaced by scar tissue. Accordingly, a significant improvement of treatment would require stopping or even reversing maladaptive remodeling as early as possible and in particular avoiding transition of hypertrophy to insufficiency.

In 1983, an inhibitor of the calcium-dependent phosphatase calcineurin, cyclosporine A, came into first clinical use as a immunosuppressive drug (Laupacis A, Keown P A, Ulan R A, McKenzie N, Stiller C R (1982) Cyclosporin A: a powerful immunosuppressant. Canadian Medical Association Journal 126: 1041-1046) that had revolutionized the transplantation of solid organs such as the kidney or the heart by effectively preventing transplant rejection. It was followed in 1994 by FK 506 (Tacrolimus) for the same purpose. Unlike cyclosporine A, Tacrolimus turned out to be especially useful as a topical crème formulation to treat patients with severe forms of atopic dermatitis and psoriasis. Today, calcineurin inhibitors, namely cyclosporine A, are used systemically to prevent transplant rejection or graft-versus-host disease upon bone marrow transplantation, and to treat chronic inflammatory diseases such as colitis ulcerosa, Chron's disease, glomerulonephritis (nephrotic syndrome), atopic dermatitis, psoriasis, rheumatoid arthritis, systemic lupus erythematosus and uveitis. In addition, cyclosporine A as eye drops, and Tacrolimus as crème formulation are used to topically treat keratitis and chronic inflammatory diseases of the skin, respectively. Moreover, there are various off-label uses for these calcineurin inhibitors. In 1991, the mechanism of action for the immunosuppressive effect of cyclosporine A, which is shared by Tacrolimus, was first described (Flanagan W M, Corthesy B, Bram R J, Crabtree G R (1991) Nuclear association of a T-cell transcription factor blocked by FK-506 and cyclosporine A. Nature 352:803-807). Both (cyclic) peptides bind to the cytoplasmic immunophilin ciclophilin, namely in T-helper cells, and the cyclosporine-ciclophilin complex in turn blocks the phosphatase activity of the calcium/calmodulin-dependent phosphatase calcineurin. Activation of the phosphatase normally results in dephosphorylation of the transcription factor(s) NFAT1-4, which in turn translocate to the nucleus where they act as co-activators, e.g. for expression of the IL2 gene. Interleukin-2 is an important autostimulatory cytokine for T-helper cells that either reinforces their clonal expansion (Th1-cells) or the release of B-lymphocyte differentiation factors such as interleukin-4 (Th2-cells). There are several additional effects that contribute to the immunosuppressive and anti-inflammatory actions of calcineurin inhibitors but blockade of downstream signaling of NFAT1-4 to the nucleus has been regarded as probably the most important mechanism of action for their clinical efficacy.

It was proposed almost two decades ago that calcium-dependent activation of calcineurin, followed by dephosphorylation of the transcription factor NFAT3 or NFATc3 is involved in inducing a pro-hypertrophic gene program in ventricular cardiomyocytes (Molkentin J D, Lu J R, Antos C L, Markham B, Richardson J, Robbins J, Grant S R, Olson E N (1998). A calcineurin-dependent transcriptional pathway for cardiac hypertrophy. Cell 93:215-228). In accordance, inhibition of calcineurin was found to block hypertrophy induction in a mouse model (Bourajjaj M, Armand A S, da Costa Martins P A, Weijts B, van der Nagel R, Heeneman S, Wehrens X H, De Windt L J (2008) NFATc2 is a necessary mediator of calcineurin-dependent cardiac hypertrophy and heart failure. Journal of Biological Chemistry 283:22295-22303). Thus, patients suffering from cardiac hypertrophy or insufficiency were treated with cyclosporine A, a calcineurin blocking agent (Parra V, Rothermel B A (2017) Calcineurin signaling in the heart: The importance of time and place. J Mol Cell Cardiol 103:121-136). However, at least for humans it has not yet been clarified how strong the activation of calcineurin must be to initiate a maladaptive remodeling process, since normal activation of the calcineurin signaling pathway actually appears to have adaptive effects (Wilkins B J, Dai Y S, Bueno O F, Parsons S A, Xu J, Plank D M, Jones F, Kimball T R, Molkentin J D (2004) Calcineurin/NFAT coupling participates in pathological, but not physiological cardiac hypertrophy. Circulation Research 94:110-118). In animal models, it was attempted to inhibit activity of the transcription factors NFAT1-4 and GATA4. E.g., in 2006, a cell penetrating and calcineurin-inhibitory peptide was developed, which was found to mimic the anti-hypertrophic effect of cyclosporin A (Kuriyama M, Matsushita M, Tateishi A, Moriwaki A, Tomizawa K, Ishino K, Sano S, Matsui H (2006) A cell-permeable NFAT inhibitor peptide prevents pressure-overload cardiac hypertrophy. Chemical Biology and Drug Design 67:238-243).

Nonetheless, efficient therapies to combat maladaptive processes in the heart are highly required, in particular therapies permitting long-term treatment and/or prevention of the process. There is, thus, a need in the art for improved methods for treating cardiac remodeling. It is therefore an objective of the present invention to provide means and methods to comply with the aforementioned needs, avoiding at least in part the disadvantages of the prior art. This problem is solved by compounds, methods, and uses of the present invention. Embodiments, which might be realized in an isolated fashion or in any arbitrary combination, are listed in the dependent claims.

Accordingly, the present invention relates to a polynucleotide comprising a Nuclear factor of activated T-cells (NFAT) binding site sequence and a reverse complement of said NFAT binding site sequence separated by a spacer sequence.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may all refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

As used herein, the term "standard conditions", if not otherwise noted, relates to IUPAC standard ambient temperature and pressure (SATP) conditions, i.e. preferably, a temperature of 25° C. and an absolute pressure of 100 kPa; also preferably, standard conditions include a pH of 7. Moreover, if not otherwise indicated, the term "about" relates to the indicated value with the commonly accepted technical precision in the relevant field, preferably relates to the indicated value ±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1%, most preferably less than 0.1% by weight of non-specified component(s). In the context of nucleic acid sequences, the term "essentially identical" indicates a percent identity value of at least 80%, preferably at least 90%, more preferably at least 98%, most preferably at least 99%. As will be understood, the term essentially identical includes 100% identity. The aforesaid applies to the term "essentially complementary" mutatis mutandis. Unless otherwise noted, amino acid and nucleotide symbols are those of WIPO standard ST.25.

The terms "Nuclear factor of activated T-cells" and "NFAT" are used herein equally to refer to the group of eukaryotic transcription factors known under this designation. Preferably, NFAT is a mammalian NFAT, more preferably a primate NFAT, most preferably a human NFAT. Preferably, NFAT is NFATc1 (NFAT2, GenBank BC112243.1), NFATc2 (NFAT1, GenBank BC144074.1), NFATc3 (NFAT4, GenBank BC001050.2), and/or NFATc4 (NFAT3, GenBank BC053855.1).

The term "polynucleotide", as used herein, refers to a linear or circular nucleic acid molecule. The polynucleotide of the invention comprises a Nuclear factor of activated T-cells (NFAT) binding site sequence and a reverse complement of said NFAT binding site sequence separated by a spacer sequence, all as specified elsewhere herein; moreover, the polynucleotide has the biological activity of binding at least one NFAT and/or causing the expression of polynucleotides binding at least one NFAT as specified herein below. The activity of a polynucleotide of binding at least one NFAT can be established by methods known in the art and as described herein in Hecker M, Wagner S, Henning S W, Wagner A H. Decoy oligodeoxynucleotides to treat inflammatory diseases. (book chapter) In: Therapeutic Oligonucleotides 2008; (ed. Kurreck J) RSC Publishing, Cambridge, U.K., pp. 163-188. Preferably, the dissociation constant $K_d$ of the NFAT/polynucleotide complex is at most $10^{-6}$ M, more preferably at most $10^{-7}$ M, even more preferably at most $10^{-8}$ M, most preferably at most $10^{-9}$ M in case the polynucleotide is a DNA, and is at most $10^{-5}$ M, more preferably at most $10^{-6}$ M, even more preferably at most $10^{-7}$ M, most preferably at most $10^{-8}$ M in case the polynucleotide is an RNA. Preferably, the binding of the polynucleotide to the NFAT polypeptide is specific; thus, preferably, the binding of the polynucleotide to a polypeptide which is not an NFAT as specified preferably is significantly weaker than binding of the polynucleotide to an NFAT. More preferably, the $K_d$ of a complex of the polynucleotide and a non-NFAT transcription factor is at least 10 fold, more preferably at least 100 fold, even more preferably at least 1000 fold higher than the $K_d$ for the NFAT/polynucleotide complex. Preferably, the polynucleotide comprises at least one of SEQ ID NOs: 1 to 18, as shown in Table 1.

| Sequence | SEQ ID NO |
|---|---|
| GAGTGGAAACATACAGCCACTGAAACA GTGGCTGTATGTTTCCACTC | 1 |
| NRWGGAAANA | 2 |
| AGTGGAAACA | 3 |
| GAGTGGAAACATACAGCCACTG | 4 |

-continued

| Sequence | SEQ ID NO |
|---|---|
| AGTGGAAAGACTTTCCACT | 5 |
| AGTGGAAACATGTTTCCACT | 6 |
| AGTGGAAACATACAGCCACT | 7 |
| AGTGGAAACCAAAGGTGA | 8 |
| AGTGGAAACAACAAAGGTGA | 9 |
| CAGAGAGGAAAAACTGTTTCATA | 10 |
| CCAAAGAGGAAAAATTGTT | 11 |
| CCAGTGGAAAGACTGTTTCAT | 12 |
| CGCCCAAAGAGGAAAATTTGTTTCATA | 13 |
| CGCCCAAAGAGGAAAATTTGTTTCATA | 14 |
| GGAGGAAAAACTGTTTCAT | 15 |
| NANWGGAAANN | 16 |
| MRTGGAAAMAWWMNKNSY | 17 |
| AGGCGCCCTGCAATATTTGCATGTCGC TATGTGTTCTGGGAAATC-ACCATAAA CGTGAAATGTCTTTGGATTTGGGAATC TTATAAGTT-CTGTATGAGACCACAGT CGACGAGTGGAAACATACAGCCACT-G AAACAGTGGCTGTATGTTTCCACTCCA CCGCAGTTTCGACCTCGAGA | 18 |

More preferably, the polynucleotide comprises a nucleic acid sequence corresponding to at least one of the consensus sequences of SEQ ID NOs: 2, 16, and 17. As is understood by the skilled person, a nucleic acid sequence corresponding to a consensus sequence may be realized by providing a polynucleotide comprising one of the specific sequences represented by the consensus sequence, by providing a polynucleotide comprising one or more nucleotides pairing with more than one nucleotide, e.g. inosine, by providing a mixture of polynucleotides each comprising one of the specific sequences represented by the consensus sequence, or a combination of the aforesaid. More preferably, the polynucleotide comprises at least one of SEQ ID NOs: 1 and 3 to 15. Most preferably, the polynucleotide comprises, preferably consists of, the sequence GAGTGGAAACATA-CAGCCACTGAAACAGTGGCTGTATGTTTCCACTC (SEQ ID NO: 1) or a sequence at least 75% identical thereto. Preferably, said sequence 75% identical to SEQ ID NO: 1 comprises at least one NFAT binding sequence as specified herein below. More preferably, the polynucleotide comprises, preferably consists of, the sequence of SEQ ID NO: 1. As will be understood, the polynucleotide preferably forms a stem-loop structure in solution, preferably in a cell, wherein the NFAT binding site sequence and its reverse complement are hybridized to form a double stranded NFAT binding site sequence.

The term "polynucleotide" encompasses single as well as partially or completely double-stranded polynucleotides. Preferably, the polynucleotide is RNA or is DNA, including cDNA.

Preferably, the polynucleotide is a DNA. The DNA polynucleotide preferably consists of or essentially consists of the NFAT binding site sequence and a reverse complement of said NFAT binding site sequence separated by a spacer sequence as specified herein. Preferably, in such case, the DNA polynucleotide comprises at least one phosphorothioate nucleotide in such case. More preferably, the DNA polynucleotide further comprises at least one promoter causing expression of an RNA comprising at least the NFAT binding site sequence, the spacer, and the reverse complement of said NFAT binding site sequence. In such case, the DNA polynucleotide in addition to the activity of binding at least one NFAT, preferably, has the additional activity of causing expression of a stem-loop RNA comprising at least an NFAT binding site sequence in a host cell. The skilled person is able to select an appropriate promoter for such purpose; preferably, the promoter is an inducible promoter, more preferably, the promoter is a constitutive promoter. Also preferably, the promoter is a cell-type specific promoter, in particular a cardiomyocyte-specific promoter.

Also preferably, the polynucleotide is an RNA. Preferably, said RNA is a short-hairpin RNA, preferably expressed or expressible from the DNA polynucleotide comprising a promoter as specified herein above. Also preferably, the RNA comprises at least one reverse transcriptase initiation site, i.e. preferably, from the RNA polynucleotide a DNA polynucleotide as specified above is expressed in a host cell comprising a reverse transcriptase.

Moreover, comprised are also chemically modified polynucleotides including naturally occurring modified polynucleotides such as glycosylated or methylated polynucleotides or artificially modified derivatives such as biotinylated polynucleotides or polynucleotides comprising phosphorothioates. The polynucleotide of the present invention shall be provided, preferably, either as an isolated polynucleotide (i.e. isolated from its natural context) or in genetically modified form. Preferably, the polynucleotide has a length of at most 1 Mb, more preferably at most 100 kb, even more preferably at most 10 kb, still more preferably at most 1 kb, most preferably at most 100 bp. Preferably, the polynucleotide is a non-naturally occurring polynucleotide; thus, preferably, the nucleotide is an artificial polynucleotide. Also preferably, the polynucleotide is a chimeric polynucleotide; more preferably, the polynucleotide comprises at least one nucleic acid sequence heterologous to the remaining nucleic acid sequences it comprises.

As used herein, the term polynucleotide, preferably, includes variants of the specifically indicated polynucleotides. More preferably, the term polynucleotide relates to polynucleotides essentially identical to the specific polynucleotides indicated. Most preferably, the term polynucleotide relates to the specific polynucleotides indicated. The term "polynucleotide variant", as used herein, relates to a variant of a polynucleotide related to comprising a nucleic acid sequence characterized in that the sequence can be derived from the aforementioned specific nucleic acid sequence by at least one nucleotide substitution, addition and/or deletion, wherein the polynucleotide variant shall have the biological activity or activities as specified for the specific polynucleotide. Thus, it is to be understood that a polynucleotide variant as referred to in accordance with the present invention shall have a nucleic acid sequence which differs due to at least one nucleotide substitution, deletion and/or addition. Preferably, said polynucleotide variant comprises an ortholog, a paralog or another homolog of the specific polynucleotide or of a functional subsequence thereof, e.g. of an NFAT binding site sequence. Also preferably, said polynucleotide variant comprises a naturally occurring allele of the specific polynucleotide or of a functional subsequence thereof. Polynucleotide variants also encompass polynucleotides comprising a nucleic acid sequence which is capable of hybridizing to the aforementioned specific polynucleotides or functional subsequences thereof, preferably, under stringent hybridization conditions. These stringent conditions are known to the skilled worker and can be found in standard textbooks. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide; accordingly, other conditions more suitable for low-G+C DNA, which are in principle known to the skilled person, may be found to be more appropriate by the skilled person. The skilled worker knows how to determine the hybridization conditions required by referring to standard textbooks. Alternatively, polynucleotide variants are obtainable by PCR-based techniques such as mixed oligonucleotide primer-based amplification of DNA, e.g. using degenerated primers. As a template, DNA or cDNA from bacteria, fungi, plants or, preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences or functional subsequences thereof. The percent identity values are, preferably, calculated over the entire nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), are preferably used. Preferably, said programs are used with their standard parameters. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences, said polynucleotide retaining the indicated activity or activities, is also encompassed as a variant polynucleotide of the present invention. A fragment as meant herein, preferably, comprises at least 30, preferably at least 40, more preferably at least 50 consecutive nucleotides of any one of the specific nucleic acid sequences and still has the indicated activity.

The polynucleotides of the present invention either consist of, essentially consist of, or comprise the aforementioned nucleic acid sequences. Thus, they may contain further nucleic acid sequences as well. Specifically, the polynucleotide of the present invention may encode e.g. polypeptides, including fusion polypeptides and selectable markers. Such fusion polypeptides may comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and are described elsewhere herein. Selectable markers are known in the art and include in particular antibiotic resistance genes, selectable metabolic markers, e.g. an auxotrophy marker, and the like. More preferably, the polynucleotide comprises at least one further transcription factor binding site sequence and a corresponding reverse complement of said at least one further transcription factor binding site sequence. In view of the above, it is clear that, preferably, the NFAT binding site sequence, the further transcription factor binding site sequence and their respective reverse complements are arranged such that the corresponding sequences hybridize under appropriate conditions. E.g. preferably, the 5' to 3' sequence is NFAT binding site sequence—further transcription factor binding site sequence—spacer sequence—reverse complement of further transcription factor binding site sequence—reverse complement of NFAT binding site sequence; or is further transcription factor binding site sequence-NFAT binding site sequence—spacer sequence—reverse complement of NFAT binding site sequence—reverse complement of further transcription factor binding site sequence. Preferably, the at least one further transcription factor binding site sequence is an NFAT binding site sequence or is a binding site sequence for at least one further transcription factor. As will be understood, a further NFAT binding site sequence may be identical to the (first) NFAT binding site sequence or may be non-identical thereto. Preferably, the further transcription factor is a further transcription factor involved in the same signaling pathway as NFAT, and/or is a transcription factor contributing to the same disease as NFAT.

Preferably, the polynucleotide further comprises at least one sequence mediating packaging of said polynucleotide into a viral particle; thus, preferably, the polynucleotide can preferably be provided packaged into a viral particle. Preferably, said viral particle is a replication-incompetent viral particle, e.g. a virus-like particle (VLP). Packaging sequences for relevant viruses are well-known in the art. Preferably, the virus is an adeno-associated virus (AAV), an adenovirus, a retrovirus, preferably a HIV-derivative, or a herpesvirus. Preferably, the virus is an adeno-associated virus; thus, preferably, the viral particle is an adeno-associated virus-like particle (AA-VLP). AA-VLPs are known in the art, including derivatives having a modified cellular tropism compared to wildtype AAV.

The term "NFAT binding site sequence", as used herein, relates to a nucleic acid sequence which, when comprised in a polynucleotide, causes at least one NFAT to bind to said polynucleotide at said nucleic acid sequence. Preferably, the NFAT binding site sequence comprises the sequence GGAAA. More preferably, the NFAT binding site sequence comprises the sequence RWGGAAANA, wherein R is A or G and W is A or T; preferably comprises the sequence NRWGGAAANA (SEQ ID NO: 2), wherein N is any base, R is A or G; and W is A or T/U; NANWGGAAANN (SEQ ID NO: 16), wherein N is any base, R is A or G; and W is A or T/U; and/or MRTGGAAAMAWWMNKNSY (SEQ ID NO: 17), wherein M is A or C, N is any base, R is A or G, W is A or T/U, K is G or T/U, S is G or C, and Y is C or T/U; more preferably comprises the sequence AGTGGAAACA (SEQ ID NO: 3). Even more preferably, the NFAT binding site sequence comprises the sequence GAGTGGAAA-CATACAGCCACTG (SEQ ID NO: 4) or a sequence at least 75% identical thereto, preferably comprises the sequence of SEQ ID NO: 4. Preferably, the sequence at least 75% identical to SEQ ID NO: 4 comprises the sequence GGAAA, more preferably the sequence RWGGAAANA, even more preferably the sequence NRWGGAAANA (SEQ ID NO: 2), most preferably the sequence AGTGGAAACA (SEQ ID NO: 3), all as specified above. Preferably, the NFAT binding site sequence has a length of from 5 to 25 nucleotides, preferably 5 to 10 nucleotides.

The term "reverse complement" of a nucleic acid sequence is understood by the skilled person. The term relates to a nucleic acid comprising the complementary bases to the original sequence in reverse order with respect to the 5'->3'orientation of a polynucleotide, such that a single-stranded polynucleotide consisting of a given sequence and a single-stranded polynucleotide consisting of its reverse complement will hybridize over their respective complete lengths under appropriate conditions. Thus, e.g. the reverse complement of the sequence 5'-GGAAA-3' is 5'-TTTCC-3'.

The term "spacer sequence", as used herein, relates to a nucleic acid neither being part of the NFAT binding site sequence nor of its reverse complement. Thus, preferably, the spacer sequence, when comprised in a polynucleotide as specified herein, hybridizes neither to the NFAT binding site sequence nor to its reverse complement. More preferably, the spacer sequence is a single-stranded sequence after the NFAT binding site sequence and its reverse complement have hybridized in the polynucleotide. Thus, preferably, the polynucleotide forms a stem-loop structure, wherein the spacer sequence is the sequence comprised in the loop. Preferably, the spacer sequence has a length of from 3 to 25 nucleotides, preferably 3 to 15 nucleotides, more preferably 3 to 10 nucleotides.

Advantageously, it was found in the work underlying the present invention that stem-loop structures chemically synthesized or expressed in a cell can be used analogously to decoy oligonucleotides. Moreover, it was surprisingly found that RNA stem-loop structures comprising appropriate sequences function as decoys for NFATs. Moreover, it was found that using these stem-loop structures, NFAT signaling and, thus, deleterious effects of calcineurin signaling, can be diminished or interrupted.

The definitions made above apply mutatis mutandis to the following. Additional definitions and explanations made further below also apply for all embodiments described in this specification mutatis mutandis.

The present invention further relates to a polynucleotide according to the present invention for use in treating and/or preventing disease.

The present invention also relates to a polynucleotide comprising a Nuclear factor of activated T-cells (NFAT) binding site sequence and a reverse complement of said NFAT binding site sequence for use in treating and/or preventing an NFAT-mediated disease. Preferably, said polynucleotide is for use in the method for treating and/or preventing NFAT-mediated disease as specified herein below.

The polynucleotide comprising an NFAT binding site sequence and a reverse complement of said NFAT binding site is a linear or circular nucleic acid molecule. Preferably, the polynucleotide comprising an NFAT binding site sequence and a reverse complement of said NFAT binding site is a double-stranded molecule, more preferably is a partly single-stranded molecule, e.g. a polynucleotide forming a stem-loop structure as specified herein above. The polynucleotide comprising an NFAT binding site sequence and a reverse complement of said NFAT binding site may, however, also be a decoy molecule, i.e. preferably, a double-stranded DNA polynucleotide comprising two single-stranded DNA molecules, the first comprising an NFAT binding site sequence and the second comprising the reverse complement of said NFAT binding site. Also, the polynucleotide comprising an NFAT binding site sequence and a reverse complement of said NFAT binding site may be a double-stranded RNA polynucleotide comprising two single-stranded RNA molecules, the first comprising an NFAT binding site sequence and the second comprising the reverse complement of said NFAT binding site. More preferably, the polynucleotide comprising an NFAT binding site sequence and a reverse complement of said NFAT binding site is a polynucleotide comprising an NFAT binding site sequence and a reverse complement of said NFAT binding site sequence separated by a spacer sequence as specified herein above.

The terms "treating" and "treatment" refer to an amelioration of the diseases or disorders referred to herein or the symptoms accompanied therewith to a significant extent. Said treating as used herein also includes an entire restoration of health with respect to the diseases or disorders referred to herein. Furthermore, the term, preferably, includes conservative treatment, i.e. treatment preventing or impeding aggravation of a disease or disorder or a symptom thereof. It is to be understood that treating, as the term is used herein, may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well-known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20%, at least 50%, at least 60%, at least 70%, at least 80%, or at least 90% of the subjects of a given cohort or population. As will be understood by the skilled person, effectiveness of treatment of e.g. cardiac remodeling is dependent on a variety of factors including, e.g. severity of existing cardiac remodeling, accompanying diseases, and further risk factors. Preferably, treating comprises decreasing inappropriate activation of NFAT in affected cells. Preferably, treating a disease or condition with a compound recited in this specification consists of a single administration of said compound within a long period of time, preferably six months, more preferably one year, most preferably two years, i.e., preferably, is a long-term treatment. More preferably, treating a disease or condition with a compound recited in this specification consists of a single administration of said compound, i.e., preferably, is a one-time treatment. The treatment, preferably, includes additional therapeutic measures, e.g. administration of calcineurin inhibitors. Preferably, in case the NFAT-mediated disease is cardiac remodeling, said treatment further comprises administration of at least one drug selected from the group consisting of ACE Inhibitors (ACEI), Beta Blockers, AT1-Inhibitors, Aldosteron Antagonists, Renin Antagonists, Diuretics, Ca-Sensitizers, Digitalis Glykosides, polypeptides of the protein S100 family, and natriuretic peptides such as BNP (Nesiritide (human recombinant Brain Natriuretic Peptide—BNP)) or ANP.

The tem "preventing" refers to retaining health with respect to the diseases or disorders referred to herein for a certain period of time in a subject. It will be understood that said period of time may be dependent on the amount of drug compound which has been administered and on individual factors of the subject discussed elsewhere in this specification. It is to be understood that prevention may not be effective in all subjects treated with the compound. However, the term requires that, preferably, a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well-known statistic evaluation tools discussed elsewhere in this specification. Preferably, preventing a disease or condition with a compound recited in this specification consists of a single administration of said compound, in particular to a subject at risk for developing said disease or condition, within a long period of time, preferably six months, more preferably one year, most preferably two years, i.e., preferably, is a long-term preventive treatment. More preferably, preventing a disease or condition with a compound recited in this specification consists of a single administration of said compound, i.e., preferably, is a one-time preventive treatment.

The term "NFAT-mediated disease", as used herein, relates to any disease or symptom caused or aggravated by and/or correlating with inappropriate activation of NFAT signaling in a tissue. Preferably, NFAT-mediated disease is selected from cardiac remodeling, i.e. preferably, pathological cardiac remodeling, in particular cardiomyopathy and/or heart failure; chronic inflammatory disease; and transplant rejection. Preferably, the NFAT-mediated disease is cardiac remodeling; thus, preferably, the tissue of inappropriate activation of NFAT signaling is a tissue of the cardiovascular system, preferably of the heart; more preferably, NFAT signaling is inappropriately activated in cardiac muscle cells (cardiomyocytes). Thus, preferably, the NFAT-mediated disease preferably is cardiac hypertrophy and/or cardiomyopathy and/or heart failure. Conditions, symptoms and diseases in which NFAT is inappropriately activated are, preferably, (i) arterial hypertension; (ii) congenital, age-related degenerative, or infection-related semilunar valve stenosis, in particular aortic valve stenosis; (iii) cardiomyopathy, in particular dilated cardiomyopathy, hypertrophic cardiomyopathy, arrhythmogenic right ventricular cardiomyopathy, left ventricular noncompaction, or restrictive cardiomyopathy; (iv) coronary heart disease; or (v) myocarditis. Preferably, coronary heart disease is associated with increased risk of myocardial infarction, more preferably myocardial infarction with subsequent cardiac remodeling (ischemic heart disease). Also preferably, the NFAT-mediated disease is chronic inflammatory disease, more preferably chronic inflammatory bowel disease, rheumatoid arthritis, systemic lupus erythematosus, glomerulosclerosis, psoriasis, or atopic dermatitis. Also preferably, the NFAT-mediated disease is transplant rejection or graft-versus-host disease, more preferably acute or chronic transplant rejection.

The present invention also relates to a viral particle comprising a polynucleotide according to the present invention. Preferably, the viral particle is a viral particle as specified herein above, more preferably a VLP as specified herein above. Thus, preferably, the viral particle is an adeno-associated VLP (AAV-VLP), preferably is an AAV9-VLP.

The present invention further relates to a method for treating and/or preventing NFAT-mediated disease in a subject suffering therefrom or expected to suffer therefrom comprising
a) administering an effective dose of the polynucleotide according to the present invention and/or a viral particle according to the present invention to said subject; and, thereby,
b) treating and/or preventing NFAT-mediated disease.

The method for treating and/or preventing NFAT-mediated disease, preferably, is an in vivo method. Moreover, it may comprise steps in addition to those explicitly mentioned above. For example, further steps may relate, e.g., to providing a polynucleotide according to the present invention for step a), or additional treatment of the NFAT-mediated disease in step b). Moreover, one or more of said steps may be performed by automated equipment.

As used herein, the term "subject" relates to a vertebrate. Preferably, the subject is a mammal, more preferably, a mouse, rat, cat, dog, hamster, guinea pig, sheep, goat, pig, cattle, or horse. Still more preferably, the subject is a primate. Most preferably, the subject is a human. Preferably, the subject is afflicted with or having an increased risk of becoming afflicted with an NFAT-mediated disease. Preferably, the subject is a graft recipient, a subject suffering from autoimmune disease, or a subject suffering from cardiovascular disease.

Preferably, the method for treating and/or preventing NFAT-mediated disease comprises topical and/or systemic application of the polynucleotide and/or the viral particle. Preferably, the topical application is epicutaneous. Systemic application, preferably, comprises transcutaneous, intraarterial, or intravenous application. As will be understood by the skilled person, the preferred mode of administration will depend on the type of NFAT-mediated disease and, thus, the target tissue; e.g. in psoriasis, administration preferably will be epicutaneous, and in cardiac remodeling, the preferred mode of administration will be intravenous or intracardial. Preferably, intraarterial or intravenous application is catheter-assisted. It is however, also envisaged that the method for treating and/or preventing NFAT-mediated disease comprises systemic administration of the polynucleotide and/or the viral particle, e.g. by intravenous infusion.

The present invention further relates to a composition comprising a polynucleotide according to the present invention and/or viral particles according to the present invention, and a carrier.

The term "composition", as used herein, relates to a mixture of compounds comprising at least a polynucleotide as specified herein and at least one carrier. The carrier(s) must be acceptable in the sense of being compatible with the other ingredients of the composition and being not deleterious to a potential recipient thereof. The carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Suitable carriers comprise those mentioned above and others well known in the art. The carrier(s) is/are selected so as not to affect the biological activity of the composition. Examples of such diluents are distilled water, physiological saline, Ringer's solutions, dextrose solution, and Hank's solution. Preferably, in the composition, at least 50%, preferably at least 75%, more preferably at least 90%, even more preferably at least 95%, most preferably essentially all viral particles are viral particles comprising a polynucleotide as specified elsewhere herein.

Preferably, the composition is a pharmaceutical composition; thus, preferably, the carrier is a pharmaceutically acceptable carrier. In addition, the pharmaceutical composition or formulation may also include other carriers, adjuvants, or nontoxic, nontherapeutic, non-immunogenic stabilizers and the like. The polynucleotide of the present invention can be formulated as a pharmaceutically acceptable salt. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well, in particular as specified elsewhere herein. Moreover, the polynucleotide can be administered in combination with other drugs either in a common pharmaceutical composition or as separated pharmaceutical compositions wherein said separated pharmaceutical compositions may be provided in form of a kit of parts. The binding polypeptide is, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

A therapeutically effective dose refers to an amount of the polynucleotide to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. The dosage regimen will be determined by the attending physician and other clinical factors; preferably in accordance with any one of the above described methods. As is well known in the medical arts, dosages for any one patient depend upon many factors, which may include the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 1 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Preferably, treating or preventing a disease or condition with a compound recited in this specification consists of a single administration of said compound.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or user's instructions in order to anticipate dose adjustments depending on the considered recipient.

The present invention further relates to the use of a polynucleotide according to the present invention and/or of viral particles according to the present invention for inhibiting at least NFAT; and the present invention relates to the use of a polynucleotide according to the present invention and/or of viral particles according to the present invention in the manufacture of a pharmaceutical composition for treating NFAT-mediated disease.

In view of the above, the following embodiments are particularly envisaged:

1. A polynucleotide comprising a Nuclear factor of activated T-cells (NFAT) binding site sequence and a reverse complement of said NFAT binding site sequence separated by a spacer sequence.

2. The polynucleotide of embodiment 1, wherein said NFAT is NFATc1 (NFAT2, GenBank BC112243.1), NFATc2 (NFAT1, GenBank BC144074.1), NFATc3 (NFAT4, GenBank BC001050.2), and/or NFATc4 (NFAT3, GenBank BC053855.1).

3. The polynucleotide of embodiment 1 or 2, wherein said NFAT binding site sequence has a length of from 5 to 25 nucleotides, preferably 5 to 10 nucleotides.

4. The polynucleotide of any one of embodiments 1 to 3, wherein the spacer sequence has a length of from 3 to 25 nucleotides, preferably 3 to 15 nucleotides, more preferably 3 to 10 nucleotides.

5. The polynucleotide of any one of embodiments 1 to 4, wherein said polynucleotide comprises at least one further transcription factor binding site sequence and a corresponding reverse complement of said at least one further transcription factor binding site sequence.

6. The polynucleotide of embodiment 5, wherein said at least one further transcription factor binding site sequence is a binding site sequence for NFAT or is a binding site sequence for at least one further transcription factor.

7. The polynucleotide of any one of embodiments 1 to 6, wherein said polynucleotide further comprises at least one sequence mediating packaging of said polynucleotide into a viral particle.

8. The polynucleotide of any one of embodiments 1 to 7, wherein said viral particle is an adeno-associated virus-like particle (VLP).

9. The polynucleotide of any one of embodiments 1 to 8, wherein said polynucleotide is comprised in a VLP, preferably an adeno-associated VLP.

10. The polynucleotide of any one of embodiments 1 to 9, wherein said polynucleotide is a recombinant polynucleotide.

11. The polynucleotide of any one of embodiments 1 to 10, wherein said polynucleotide is a DNA.

12. The polynucleotide of embodiment 11, wherein said DNA comprises at least one promoter causing expression of at least the NFAT binding site sequence, the spacer, and the reverse complement of said NFAT binding site sequence as an RNA.

13. The polynucleotide of embodiment 11, wherein said DNA is a short-hairpin DNA, preferably having a length of from 15 to 50 nucleotides.

14. The polynucleotide of embodiment 13, wherein said DNA comprises at least one phosphothioester bond.

15. The polynucleotide any one of embodiments 1 to 10, wherein said polynucleotide is an RNA.

16. The polynucleotide of embodiment 15, wherein said RNA is a short-hairpin RNA.

17. The polynucleotide of embodiment 15 or 16, wherein said RNA comprises at least one reverse transcriptase initiation site.

18. The polynucleotide of any one of embodiments 1 to 17, wherein said NFAT binding site sequence comprises the sequence GGAAA.

19. The polynucleotide of any one of embodiments 1 to 18, wherein said NFAT binding site sequence comprises the sequence RWGGAAANA, wherein R is A or G and W is A or T/U; preferably comprises the sequence NRWGGAAANA (SEQ ID NO: 2), wherein N is any base, R is A or G and W is A or T; more preferably comprises the sequence AGTGGAAACA (SEQ ID NO: 3).

20. The polynucleotide of any one of embodiments 1 to 19, wherein said NFAT binding site sequence comprises the sequence GAGTGGAAACATACAGCCACTG (SEQ ID NO: 4) or a sequence at least 75% identical thereto, preferably comprises the sequence of SEQ ID NO: 4.

21. The polynucleotide of any one of embodiments 1 to 20, wherein the polynucleotide comprises, preferably consists of, the sequence GAGTGGAAACATACAGCCACTGAAACAGTGGCTGTATGTTTCCACTC (SEQ ID NO: 1) or a sequence at least 75% identical thereto, preferably comprises the sequence of SEQ ID NO: 1.

22. A polynucleotide according to any one of embodiments 1 to 21 for use in treating and/or preventing disease.

23. A polynucleotide comprising a Nuclear factor of activated T-cells (NFAT) binding site sequence and a reverse complement of said NFAT binding site sequence for use in treating and/or preventing an NFAT-mediated disease.

24. The polynucleotide for use of embodiment 23, wherein said NFAT-mediated disease is selected from cardiac remodeling, in particular cardiomyopathy and/or heart failure; chronic inflammatory disease; and transplant rejection.

25. The polynucleotide for use of embodiment 23 or 24, wherein said cardiac remodeling is caused by (i) arterial hypertension; (ii) congenital, age-related degenerative, or infection-related semilunar valve stenosis, in particular aortic valve stenosis; (iii) cardiomyopathy, in particular dilated cardiomyopathy, hypertrophic cardiomyopathy, arrhythmogenic right ventricular cardiomyopathy, left ventricular noncompaction, or restrictive cardiomyopathy; (iv) coronary heart disease; or (v) myocarditis.

26. The polynucleotide for use of any one of embodiments 23 to 25, wherein said coronary heart disease is associated with increased risk of myocardial infarction, preferably myocardial infarction with subsequent cardiac remodeling (ischemic heart disease).

27. The polynucleotide for use of any one of embodiments 23 to 26, wherein said chronic inflammatory disease is chronic inflammatory bowel disease, rheumatoid arthritis, systemic lupus erythematosus, glomerulosclerosis, psoriasis, or atopic dermatitis.

28. The polynucleotide for use of embodiment 23 or 24, wherein said NFAT-mediated disease is acute or chronic transplant rejection.

29. The polynucleotide for use of any one of embodiments 23 to 28, wherein said polynucleotide is a polynucleotide according to any one of embodiments 1 to 21.

30. A viral particle comprising a polynucleotide according to any one of embodiments 1 to 23.

31. The viral particle of embodiment 30, wherein said viral particle is an adeno-associated VLP (AAV-VLP), preferably is an AAV9-VLP.

32. A method for treating and/or preventing NFAT-mediated disease in a subject suffering therefrom or expected to suffer therefrom comprising
a) administering an effective dose of polynucleotide according to any one of embodiments 1 to 23 and/or a viral particle according to embodiment 30 or 31 to said subject; and, thereby,
b) treating and/or preventing NFAT-mediated disease.

33. The method of embodiment 32, wherein said NFAT-mediated disease is selected from cardiac remodeling, in particular cardiomyopathy and/or heart failure; chronic inflammatory disease; and transplant rejection.

34. The method of embodiment 32 or 33, wherein said cardiac remodeling is caused by (i) arterial hypertension; (ii) congenital, age-related degenerative, or infection-related semilunar valve stenosis, in particular aortic valve stenosis; (iii) cardiomyopathy, in particular dilated cardiomyopathy, hypertrophic cardiomyopathy, arrhythmogenic right ventricular cardiomyopathy, left ventricular noncompaction, or restrictive cardiomyopathy; (iv) coronary heart disease; or (v) myocarditis.

35. The method of any one of embodiments 32 to 34, wherein said coronary heart disease causes myocardial infarction, preferably myocardial infarction with subsequent cardiac remodeling (ischemic heart disease).

36. The method of any one of embodiments 32 to 35 comprising topical and/or systemic application, preferably epicutaeous, transcutaenous, intraarterial, or intravenous application, of said polynucleotide according to any one of embodiments 1 to 23 and/or said viral particle according to embodiment 30 or 31, preferably wherein said intraarterial or intravenous application is catheter-assisted.

37. A composition comprising a polynucleotide according to any one of embodiments 1 to 21 and/or viral particles according to embodiment 30 or 31, and a carrier.

38. A composition comprising the viral particle according to embodiment 30 or 31 and a carrier, wherein at least 50%, preferably at least 75%, more preferably at least 90%, even more preferably at least 95%, most preferably essentially all viral particles are viral particles according to embodiment 30 or 31.

39. The composition of embodiment 37 or 38, wherein the composition is a pharmaceutical composition and wherein said carrier is a pharmaceutically acceptable carrier.

40. Use of a polynucleotide according to any one of embodiments 1 to 21 and/or of viral particles according to any one of embodiments 30 to 33 for inhibiting at least NFAT.

41. Use of a polynucleotide according to any one of embodiments 1 to 23 and/or of viral particles according to embodiment 30 or 31 in the manufacture of a pharmaceutical composition for treating NFAT-mediated disease.

42. The subject matter of any of the preceding embodiments, wherein said NFAT binding site lies in the 5'-untranscribed region of at least 50%, more preferably at least 80%, even more preferably at least 90%, most preferably all, NFAT target genes.

All references cited in this specification are herewith incorporated by reference with respect to their entire disclosure content and the disclosure content specifically mentioned in this specification.

FIGURE LEGENDS

FIG. 1: Naked hairpin consensus NFAT decoy ODN (hpNFATcons) but not the mutant control ODN (hpNFATmut) inhibits induction by ET-1 of the fetal gene program in HL-1 cells. (A) Messenger RNA levels of ANP and BNP were analysed in HL-1 cardiomyocytes as markers of the ET-1 (100 nmol/L) induced hypertrophic response. Gene expression was normalized to RPL32 as a housekeeping gene. (B) BNP protein levels were measured in HL-1 cells supernatants and lysates using ELISA and expressed relative to the concentration measured in non-stimulated control cells. (n=4, * p<0.05 as indicated).

Figure 2:
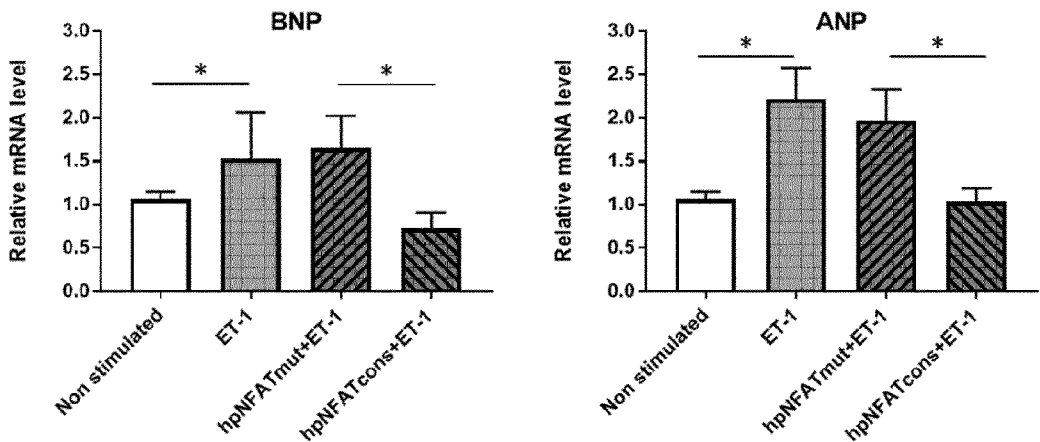

FIG. 2: Naked hairpin consensus NFAT decoy ODN (hpNFATcons) but not the mutant control ODN (hpNFATmut) inhibits induction by ET-1 of the fetal gene program also in murine neonatal cardiomyocytes. Summary data for ANP and BNP mRNA levels in neonatal cardiomyocytes as indicated. RPL32 was used for normalization of mRNA levels and non-stimulated neonatal cardiomyocytes served as a control. (n=4, * p<0.05 as indicated).

Figure 3:
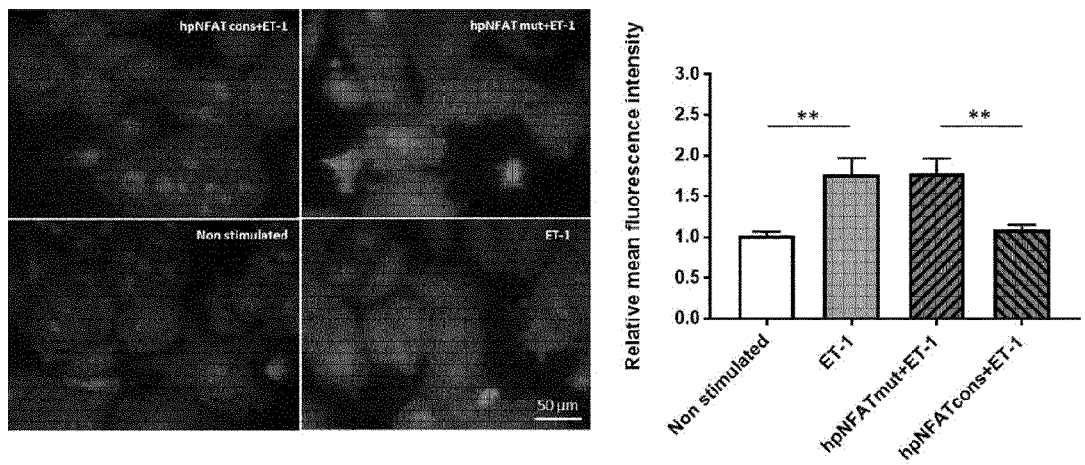

FIG. 3: Naked hairpin consensus NFAT decoy ODN (hpNFATcons) but not the mutant control ODN (hpNFATmut) blocks upregulation by ET-1 of protein translation in HL-1 cells. (Left) Representative images showing puromycin staining in cardiac tissue sections from the different treatment groups. A Cy5-labelled secondary antibody (grey fluorescence) was used and nuclei were stained with DAPI (light grey fluorescence). (Right) The graph summarizes the statistical quantification of mean fluorescence intensity in the indicated treatment groups. (n=4 with 20 images analyzed/treatment group, ** p<0.01 as indicated).

Figure 4:
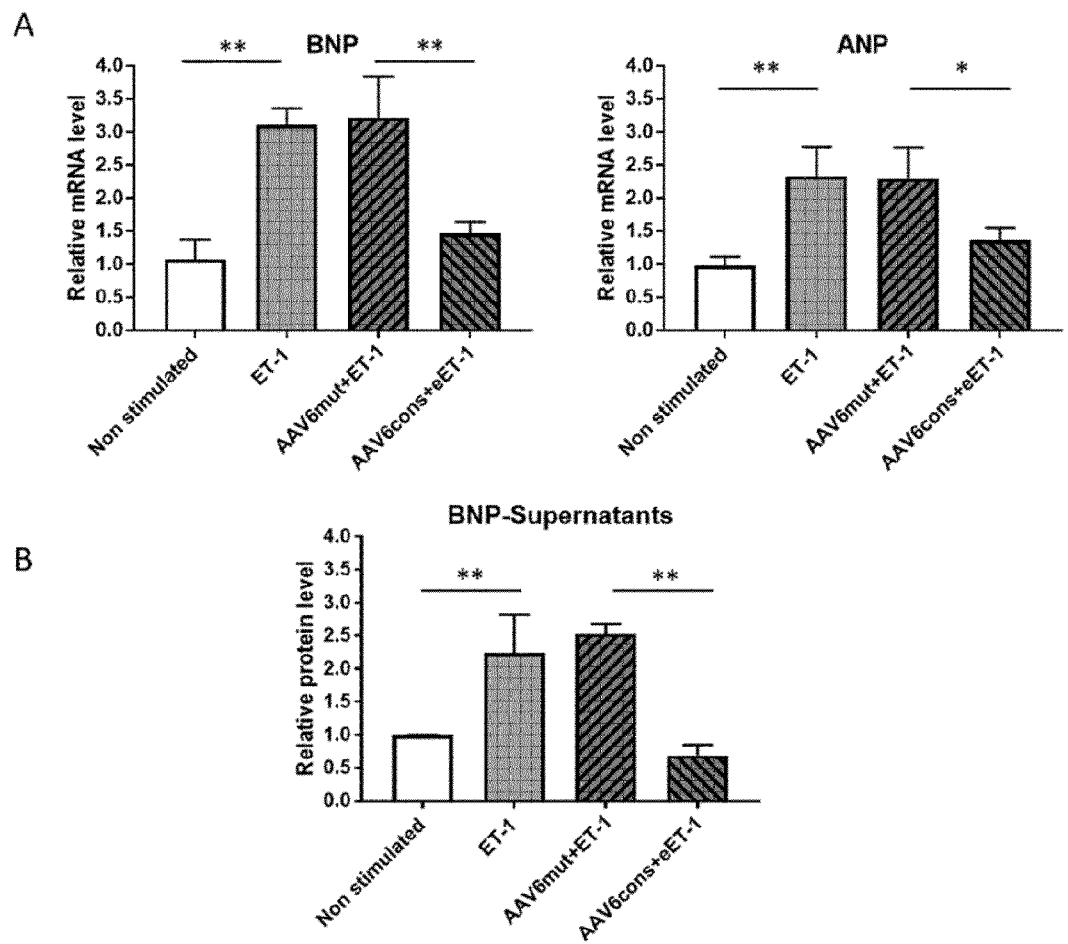

FIG. 4: AAV6-mediated delivery of consensus hpNFAT RNA decoy ODN (AAV6cons) but not the mutant control ODN (AAV6mut) inhibits induction by ET-1 of the fetal gene program in HL-1 cells. (A) ANP and BNP mRNA levels were analyzed in HL-1cells that had been transduced with the RNA decoy ODN-expressing viral vectors. RPL32 was used as a housekeeping gene. (n=5, * p<0.05, ** p<0.01 as indicated) (B) BNP protein levels in the supernatant of the cardiomyocyte cell line were determined by ELISA and values normalized to the BNP concentration in the supernatant of non-stimulated control cells. (n=4, * p0.05, ** p<0.01 as indicated).

Figure 5:
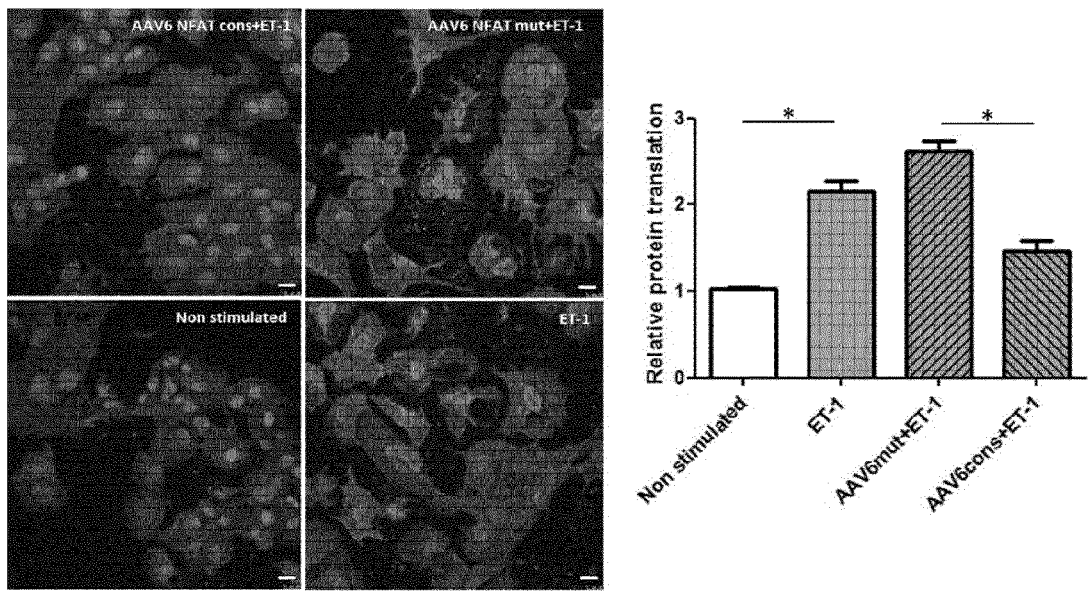

FIG. 5: AAV6-mediated delivery of consensus hpNFAT RNA decoy ODN (AAV6cons) but not the mutant control ODN (AAV6mut) inhibits induction by ET-1 of the rate of protein translation in the HL-1 cells. (Left) Representative images showing puromycin staining in cardiac tissue sections from the different treatment groups. A Cy5-labelled secondary antibody (grey fluorescence) was used and nuclei were stained with DAPI (light grey fluorescence). The scale bar represents 10 μm. (Right) The graph summarizes the statistical quantification of mean fluorescence intensity in the indicated treatment groups. (n=4 with 20 images analyzed/treatment group, * p<0.01 as indicated).

Figure 6:
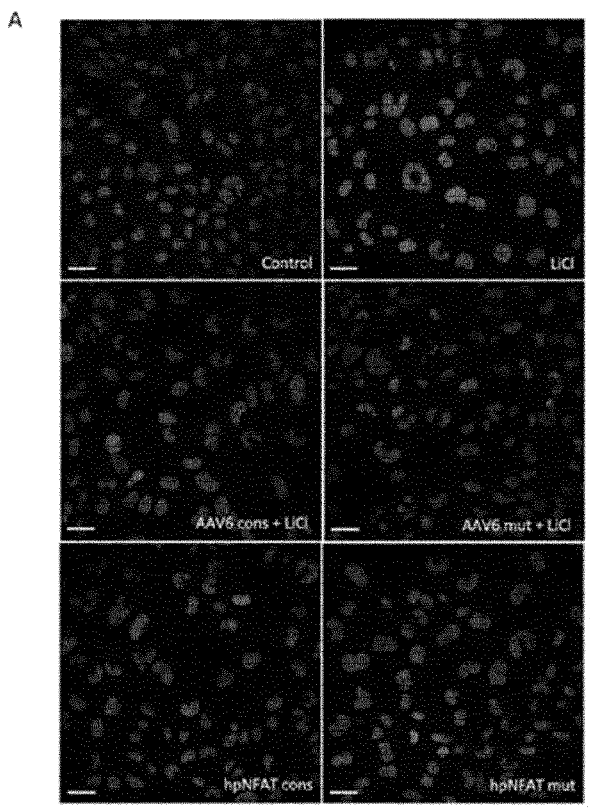
Figure 6:
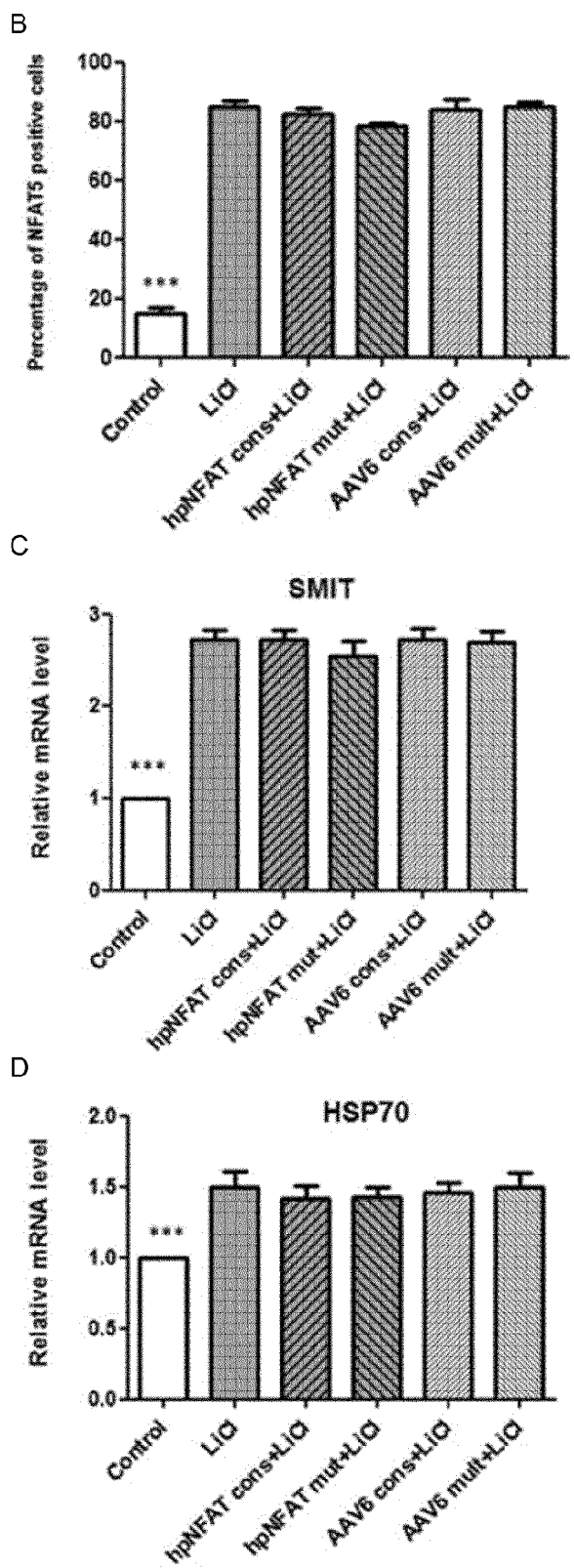

FIG. 6: Neither the naked hairpin DNA (hpNFATcons) nor the AAV6-transduced hairpin RNA decoy ODN (AAV6cons) affect NFAT5 translocation and function in HL-1 cells subjected to hyperosmotic stress. (A, B) Analysis of NFAT5 distribution in HL-1 cells subjected to hyperosmotic stress (100 mmol/L LiCl). The graph in B) summarizes quantification by immunofluorescence analysis of NFAT5-positive nuclei (grey fluorescence) marked in addition with DAPI (light grey fluorescence). The scale bar represents 25 μm. (n=4 with 20 images analyzed/group, * p<0.001 vs. all other treatment groups) (C,D) Quantitative RT-PCR analysis (summary data) of NFAT5 target gene products SMIT (sodium/myoinositol cotransporter) and HSP70 (heat shock protein 70). RPL32 was used as a housekeeping gene and mRNA values were normalized to the mRNA level determined in untreated control cells. (n=4,  p<0.01 vs. all other treatment groups).

Figure 7:
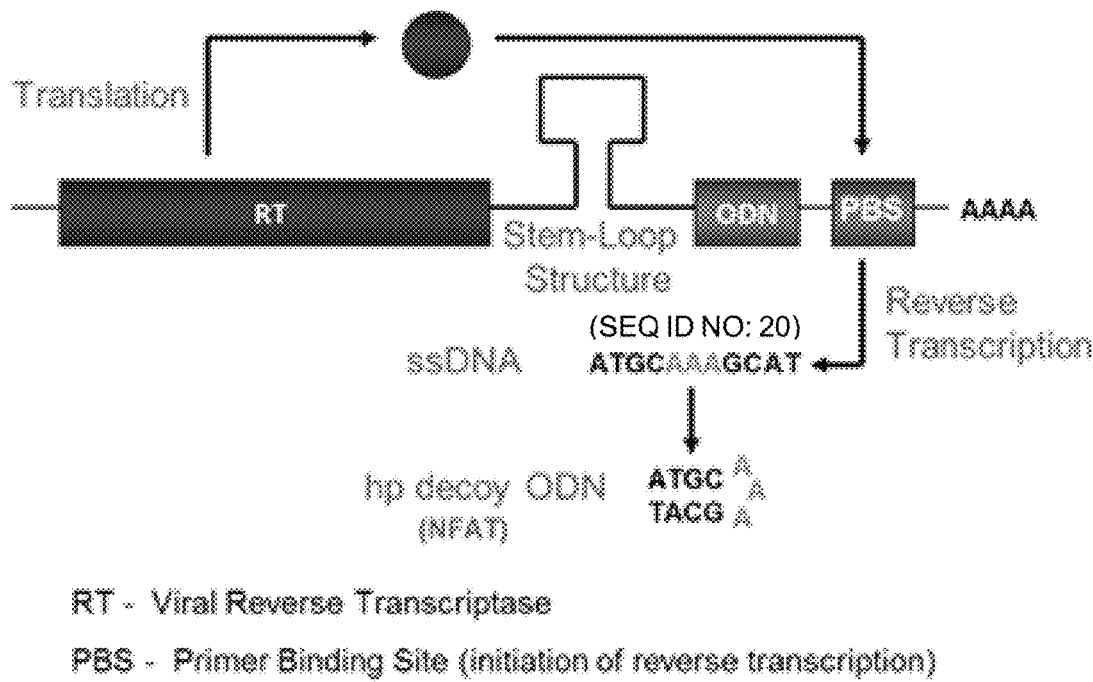
Figure 7:
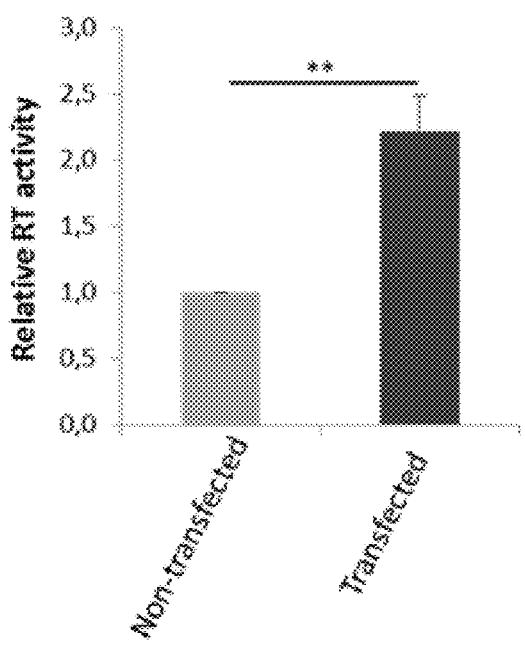

FIG. 7: Principle of the expression of a cDNA-based consensus hpNFAT decoy ODN in cardiomyocytes and confirmation of successful transfection of HL-1 cells with the plasmid-based expression construct. (Upper panel) The figure illustrates the principle of the approach taken. (Lower panel) Reverse transcriptase (RT) is expressed by HL-1 cells 2 days post transfection. RT activity in the HL-1 cells was determined by using the C-Type Reverse Transcriptase activity kit from Cavidi, Uppsala, Sweden. (n=4, ** p<0.01 as indicated); The sequence shown is SEQ ID NO: 20.

Figure 8:
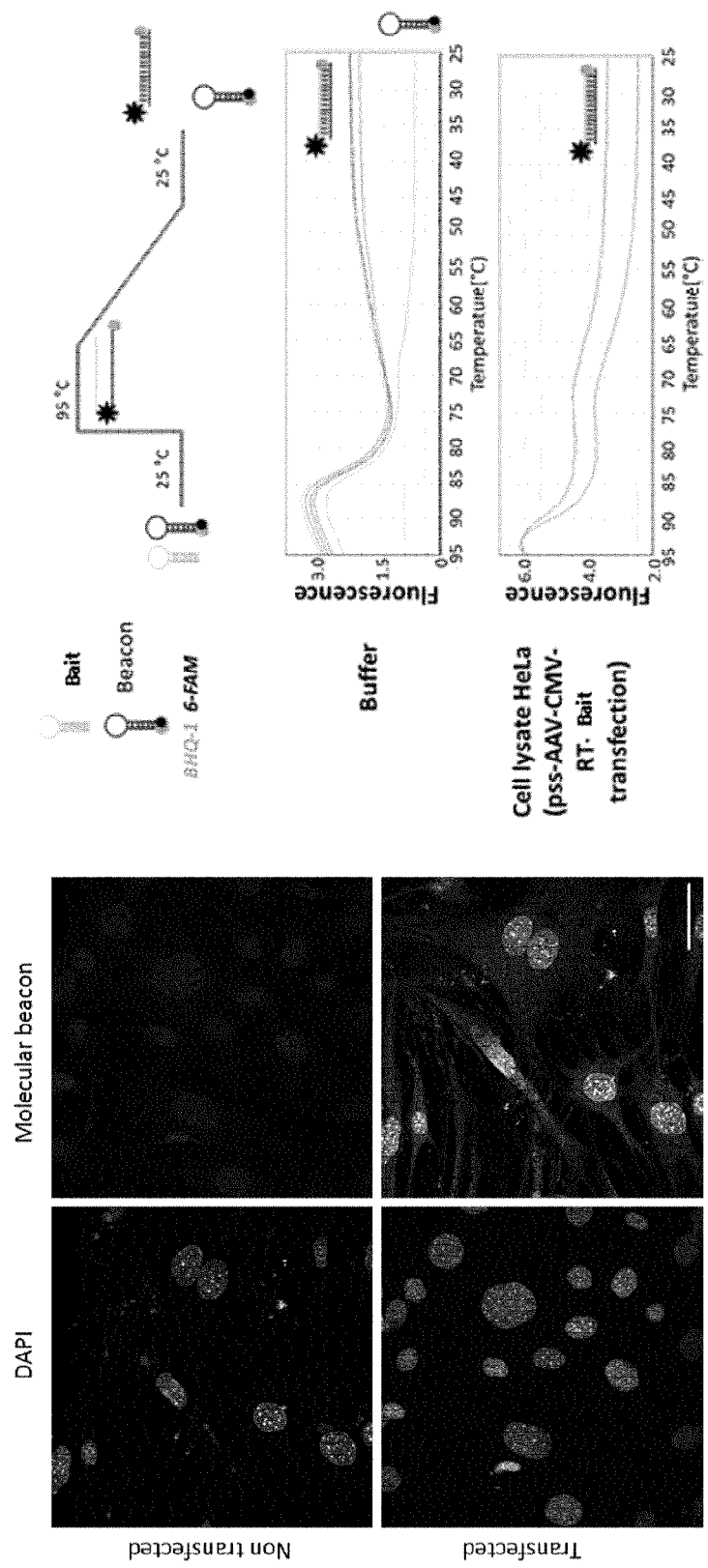

FIG. 8: Principle of the molecular beacon technique and detection of an expressed cDNA-based consensus bait decoy ODN in HeLa cells. The cells were transfected with a plasmid harboring a CMV promotor-driven reverse transcriptase/consensus bait decoy ODN expression construct. A molecular beacon complementary to the expressed and reverse transcribed single-stranded cDNA bait molecule, labeled with the fluorophore 6-carboxyfluorescein (6-FAM) at the 5' end and the black hole quencher-1 (BHQ-1) at the 3' end, was added to the fixed cells or lysates thereof 2 days post transfection overnight. (Left panel) Detection of the decoy ODN mostly in the nucleus and in part in the cytoplasm of the HeLa cells 2 days post transfection by using the molecular beacon Nuclei were counterstained with DAPI, the scale bar corresponds to 15 μm, shown is a representative experiment. (Right panel) The figure illustrates the principle of the molecular beacon technique (top) and a typical readout (bottom) for the cDNA-based bait decoy ODN present in lysates of the HeLa cells 2 days post transfection and overnight incubation with the molecular beacon. For the latter, samples (cell lysate) were placed in glass capillaries in a LightCycler 2.0 instrument and heated to 95° C. followed by a cool-down phase to 25° C. while continuously recording fluorescence emission at 517 nm.

Figure 9:
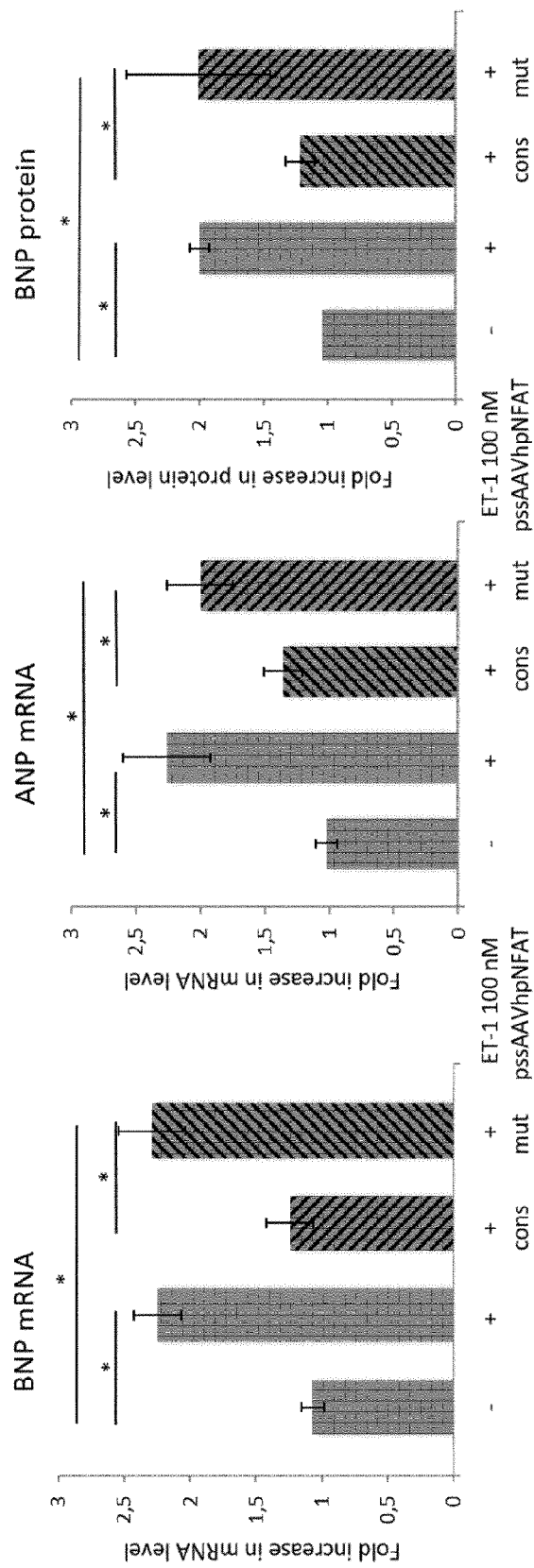

FIG. 9: Plasmid-mediated delivery of the cDNA-based consensus hpNFAT decoy ODN but not the mutant control ODN to HL-1 cells for 2 days inhibits induction by ET-1 (100 nmol/L, 24 hours) of the fetal gene program. ANP and BNP mRNA levels were determined by qRT-PCR, BNP protein abundance by ELISA. (n=5, * p<0.05 as indicated).

Figure 10:
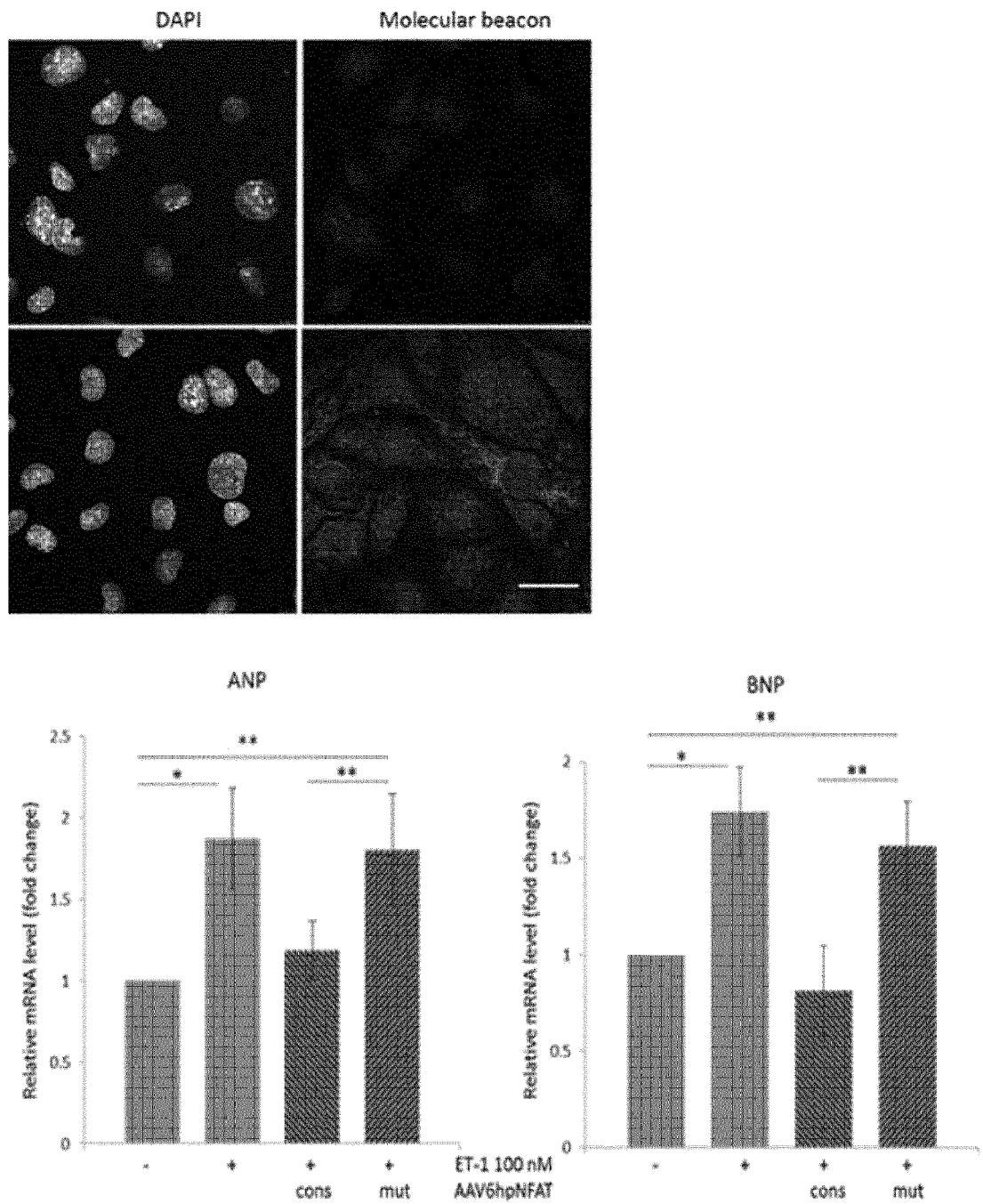

FIG. 10: AAV6-mediated delivery of the cDNA-based consensus hpNFAT decoy ODN but not the mutant control ODN to HL-1 cells for 3 days inhibits induction by ET-1 (100 nmol/L, 24 hours) of the fetal gene program. (Upper panel) Detection of the decoy ODN in the nucleus and in part in the cytoplasm of HL-1 cells 3 days post transduction with the viral vector by using the molecular beacon technique. Nuclei were counterstained with DAPI, the scale bar corresponds to 15 µm, shown is a representative experiment. (Lower panel) ANP and BNP mRNA levels were determined by qRT-PCR. (n=6, * p<0.05, p<0.01 as indicated).

Figure 11:
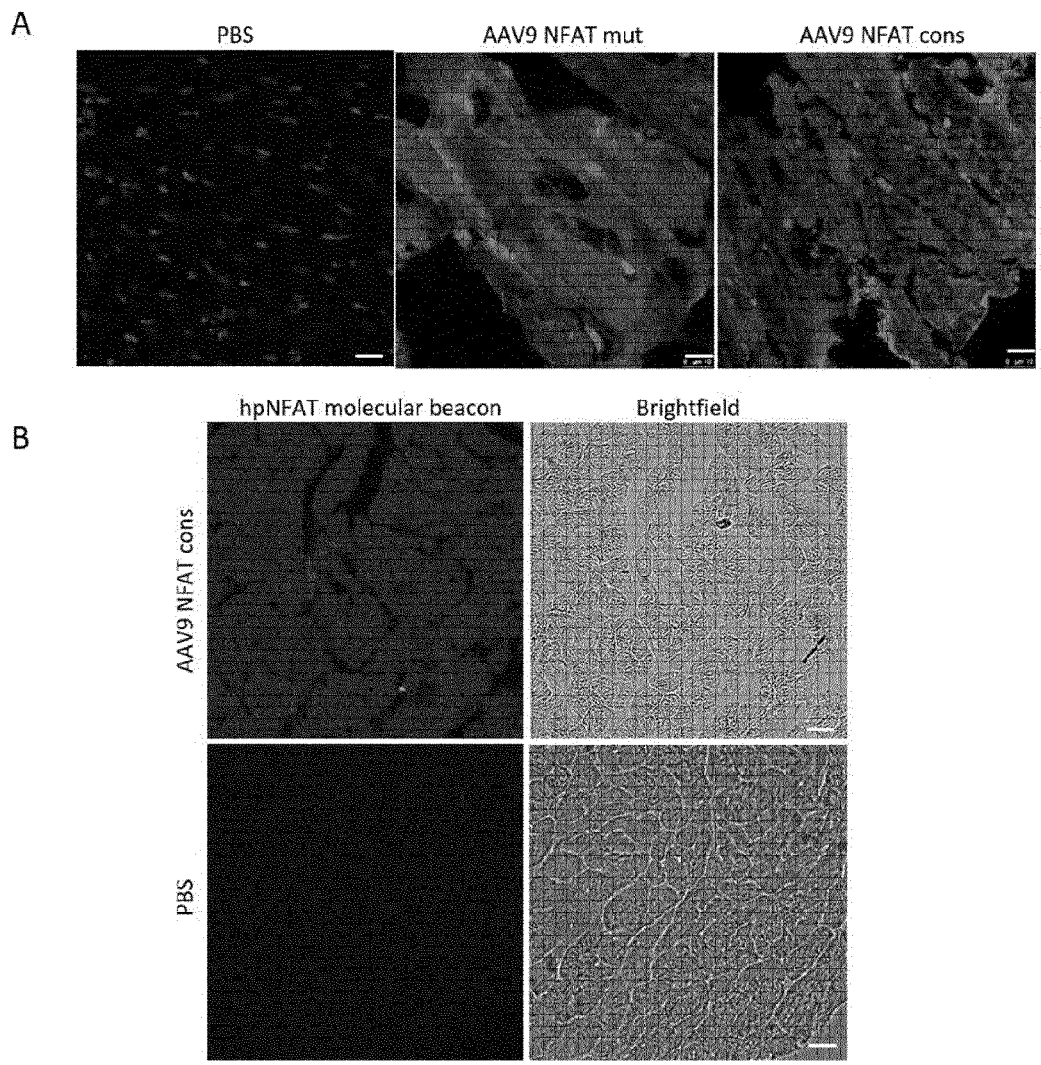

FIG. 11: Transduction efficiency in cardiomyocytes of AAV9 injected mice, 2 weeks after virus injection. (A) Representative images showing EGFP immunohistochemistry (green fluorescence) performed in heart cryosections. (B) Detection of the hpNFAT consensus RNA decoy ODNs in heart cryosections by F.I.S.H. Red fluorescence corresponds to hybridization of the probe to the target and proves generation of the decoy ODNs in situ. Scale bar represents 10 µm. (n=3 for PBS injected mice, n=8 for AAV9 injected groups, exemplary pictures).

Figure 12:
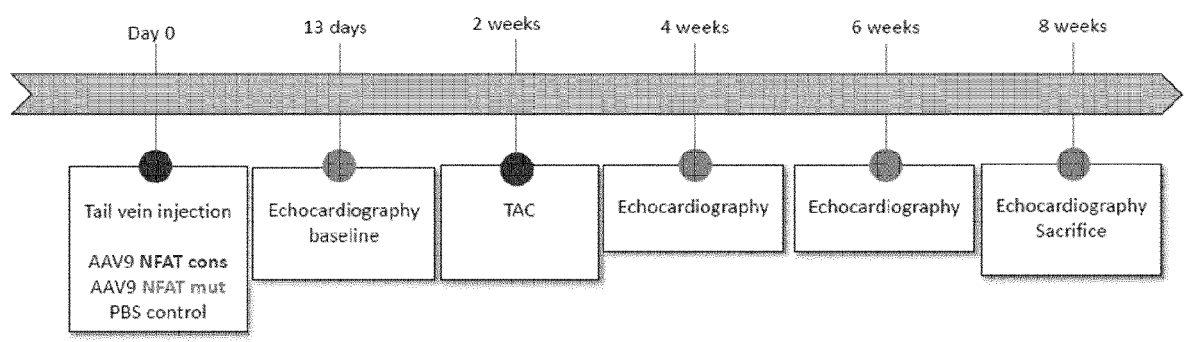

FIG. 12: Scheme of the work flow for the animal proof-of-concept model used (prevention study).

Figure 13:
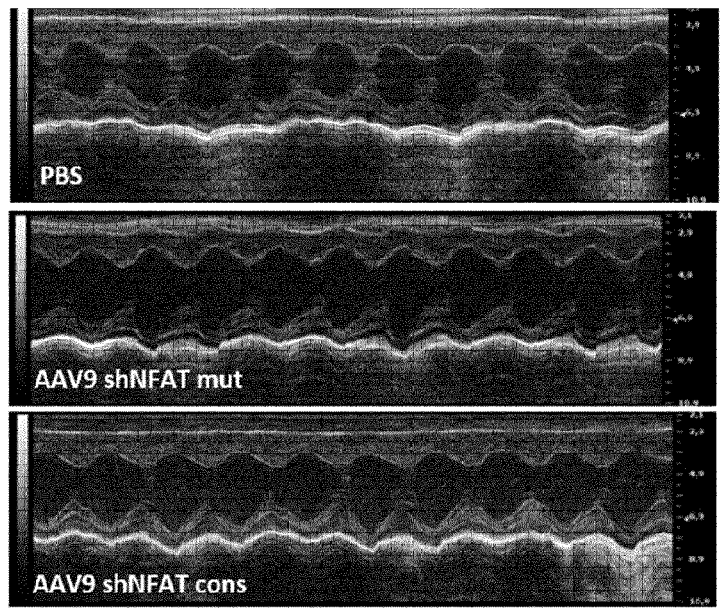
Figure 13:
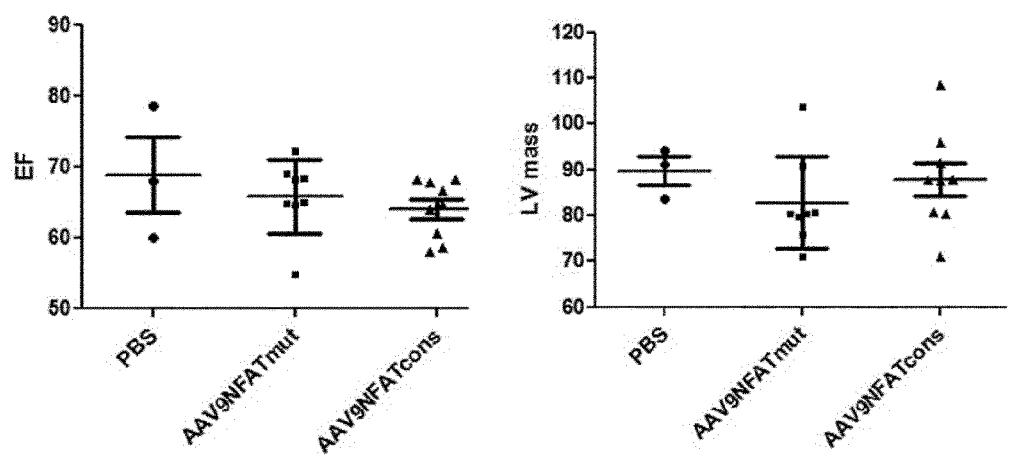

FIG. 13: Echocardiographic assessment of heart function in AAV9 injected mice prior to hypertrophy induction by TAC. Representative M-mode echocardiograms and analysis of ejection fraction as a functional cardiac parameter and left ventricular mass at baseline. EF: ejection fraction; LV: left ventricle. (n=3 for PBS injected group, n=8 for AAV9 injected groups).

Figure 14:
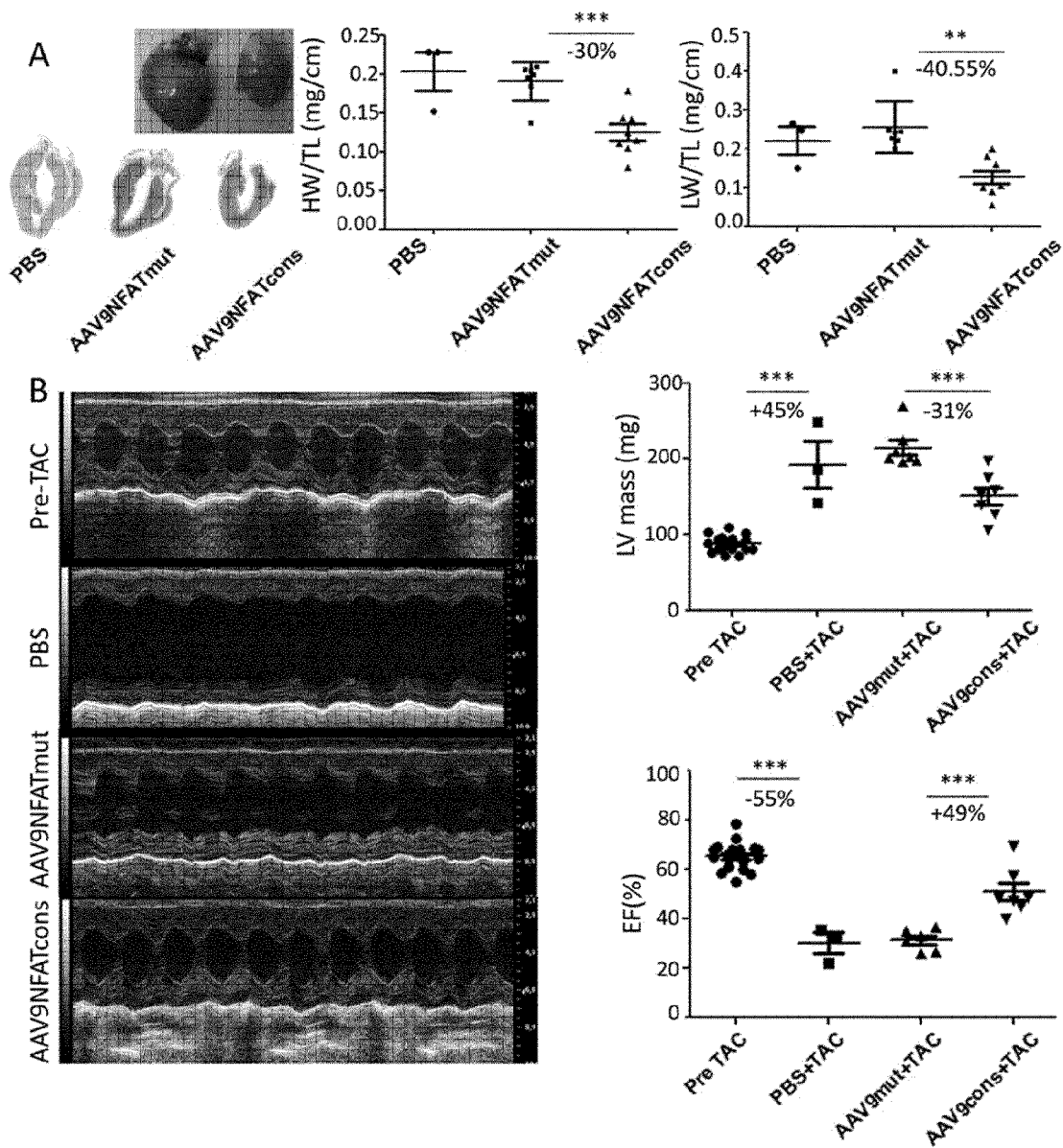

FIG. 14: AAV9-mediated generation of hpNFAT consensus RNA decoy ODNs decreases TAC-induced heart hypertrophy. (A) The graphs summarizes the statistical quantification of markers of heart hypertrophy (HW/TL) and heart failure (LW/TL). The images on the left show gross morphology of the different AAV9 injected groups after TAC. (n=3 for PBS injected group, n=8 for AAV9 injected groups,  p<0.01). (B) Representative M-mode echocardiograms of control mice and of animals subjected to TAC. On the right, the graphs present the statistical analyses of calculated LV (left ventricular) mass and EF (ejection fraction). (n=3 for PBS injected group, n=8 for AAV9 injected groups  p<0.01; HW: heart weight, TL: tibia length, LW: lung weight, EF: ejection fraction).

Figure 15:
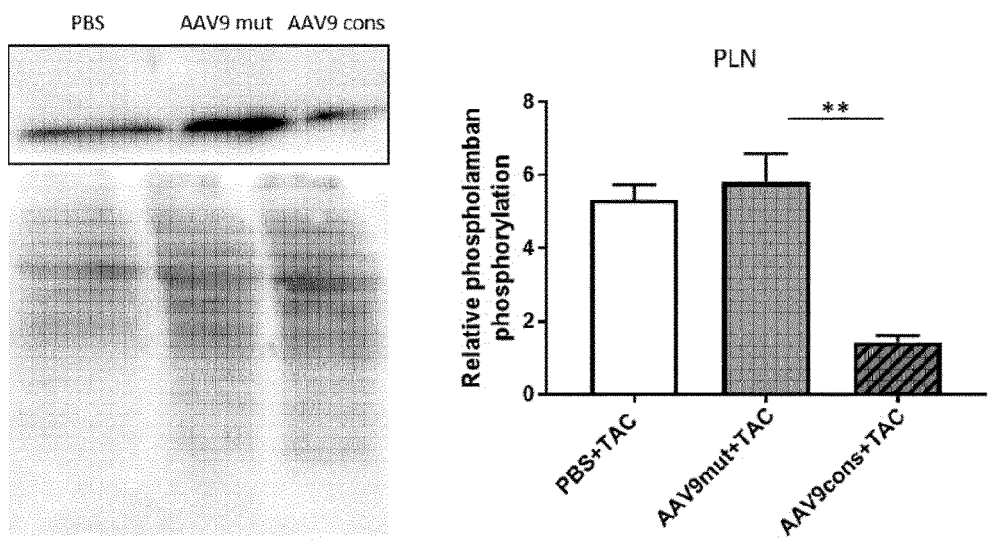

FIG. 15: AAV9-mediated expression of hpNFAT consensus RNA decoy ODNs decreases the phosphorylation level of phospholamban (PLN) at Ser16 in heart tissue. Western blot analysis using a specific antibody that recognizes the phosphorylated PLN at Ser16. Ponceau S staining was used as a loading control. (n=3, ** p<0.01).

Figure 16:
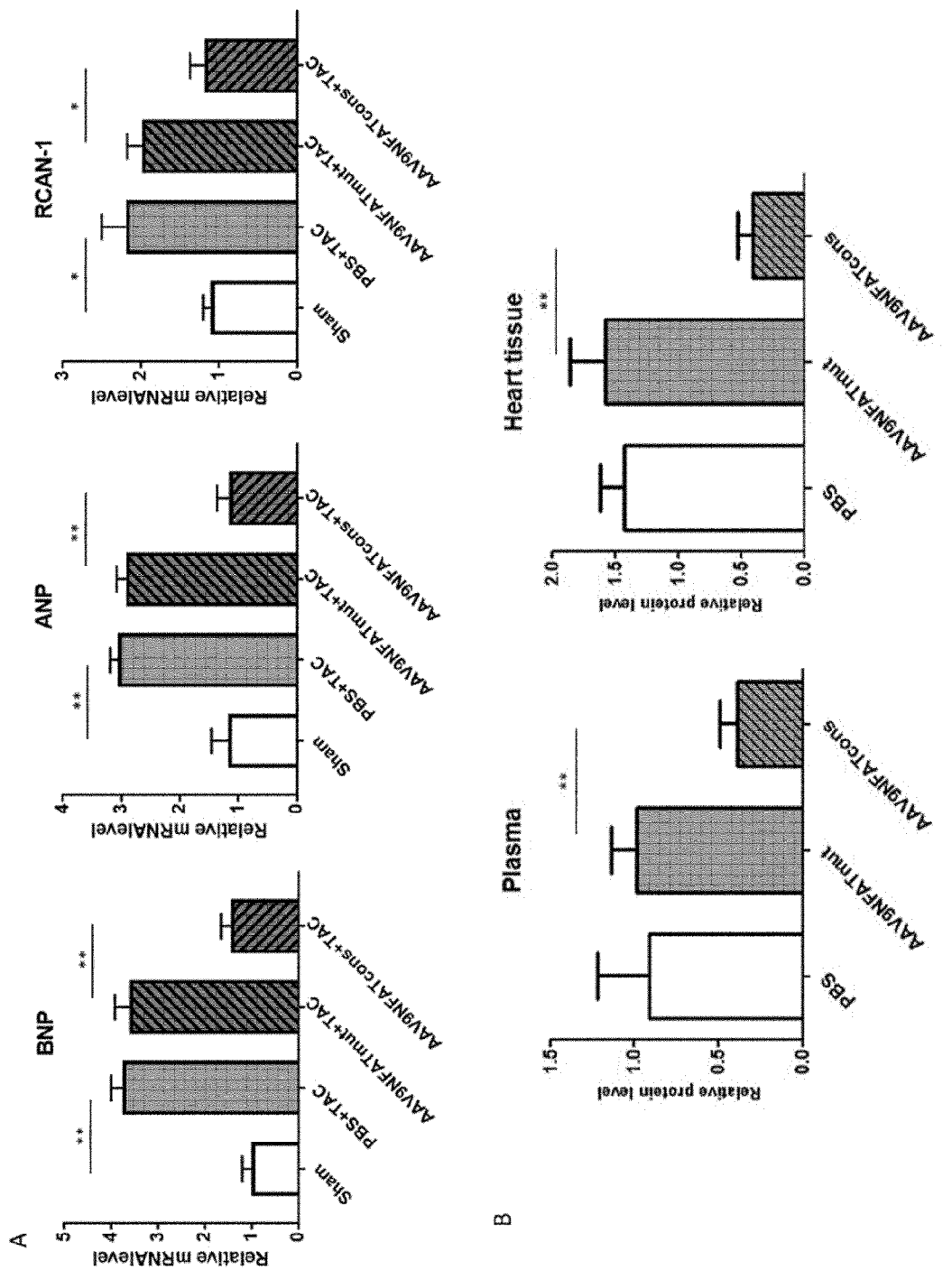

FIG. 16: AAV9-mediated delivery of hpNFAT consensus RNA decoy ODNs into the myocardium decreases the expression of TAC-induced pro-hypertrophic markers. (A) Gene expression analysis of ANP, BNP and ROAN-1 in the heart tissue, using RPL32 as a housekeeping gene. Values were normalized to sham-operated mice as control. (B) BNP protein level was measured by ELISA in plasma and heart protein extracts. (n=3 for sham and PBS injected groups, n=8 for AAV9 injected groups, * p<0.05, ** p<0.01).

Figure 17:
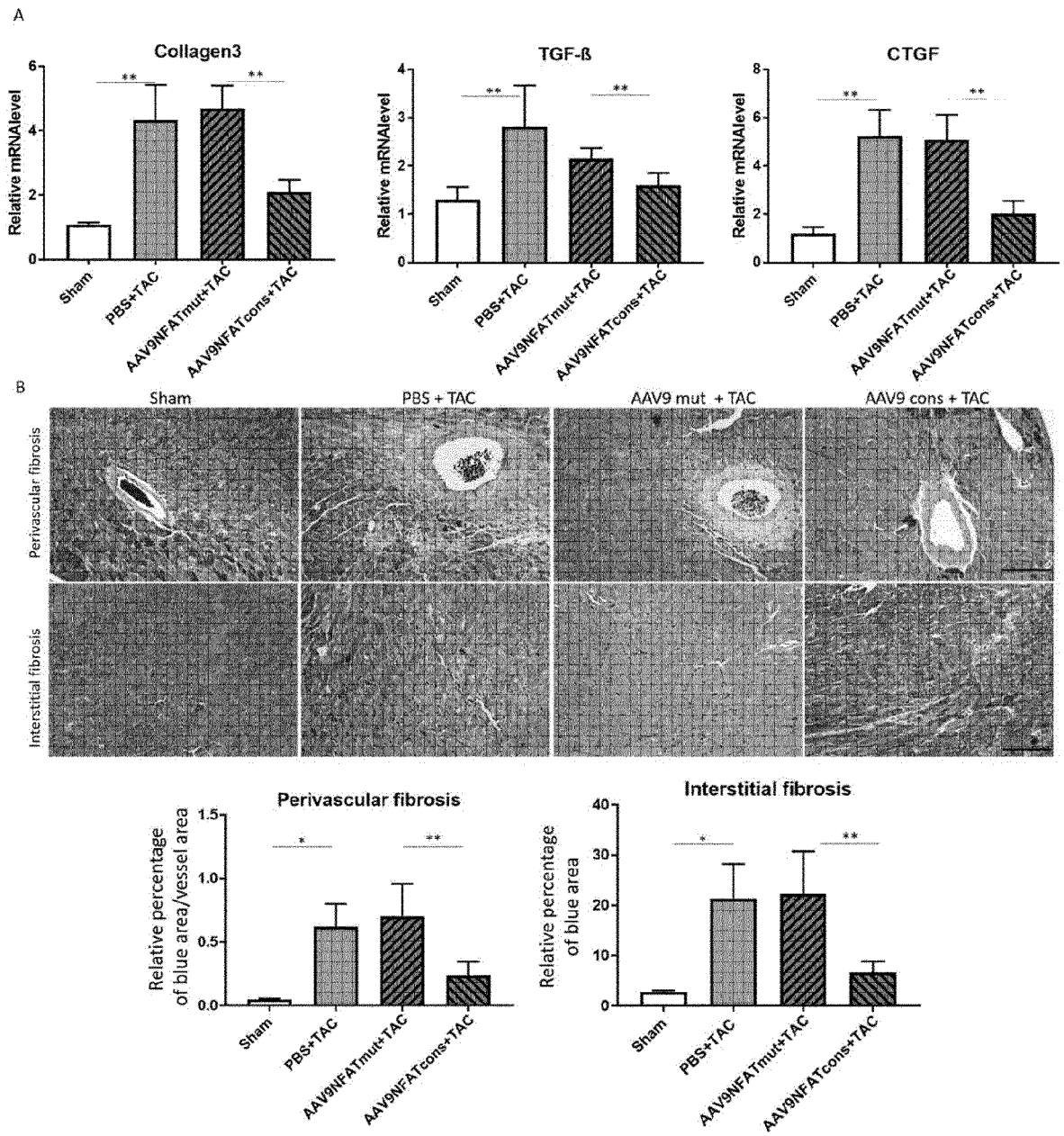

FIG. 17: AAV9-mediated delivery of hpNFAT consensus RNA decoy ODNs into the myocardium decreases fibrosis markers in heart sections. (A) mRNA levels of fibrosis markers collagen-3, TGF-β and CTGF in cardiac tissue. Gene expression was normalized to RPL32 as a housekeeping gene (n=3 for sham and PBS injected groups, n=8 for AAV9 injected groups, * p<0.05, ** p<0.01). (B) Representative left ventricular cross sections revealing perivascular and interstitial fibrosis. The graphs present the statistical quantification of the percentage of fibrosis (blue area) in the myocardium of mice from the different treatment groups. Scale bar represents 20 µm. (n=3 for sham and PBS injected groups, n=8 for AAV9 injected groups, * p<0.05, ** p<0.01).

Figure 18:
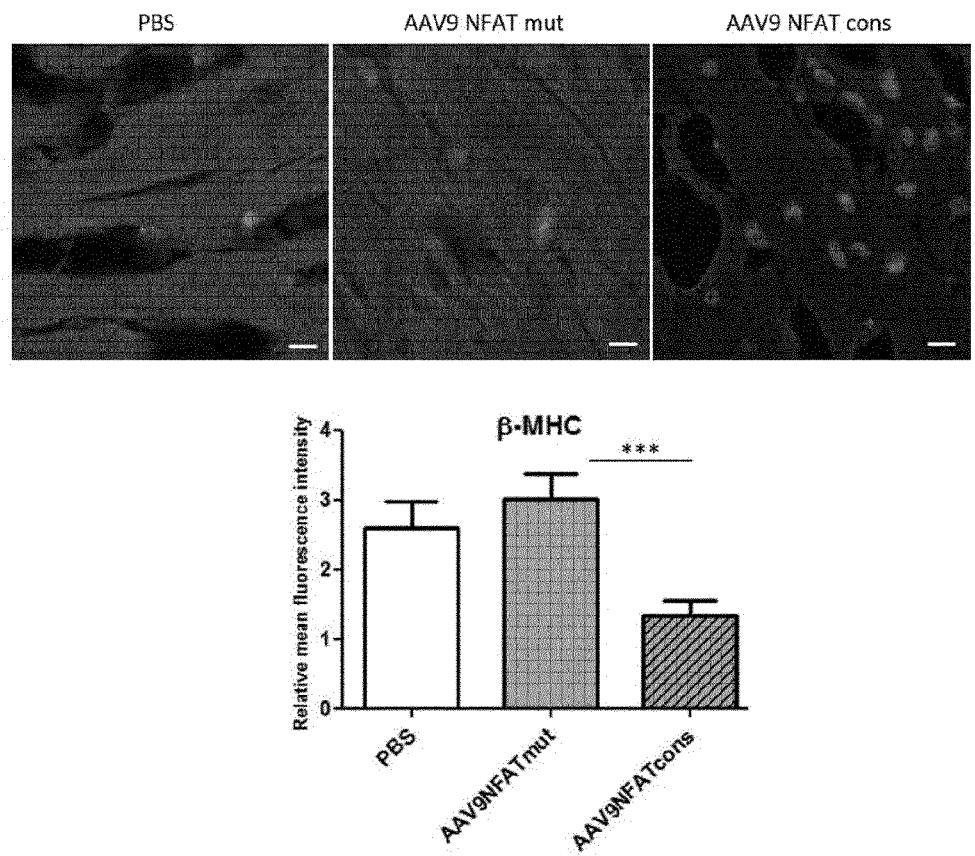

FIG. 18: AAV9-mediated delivery of hpNFAT consensus RNA decoy ODNs into the myocardium reduces β-MHC protein level. Representative images depicting β-MHC immunohistochemistry (red fluorescence) in heart cryosections. Nuclei were stained with DAPI (blue). The graph shows the statistical summary of the quantification of mean red fluorescence intensity in the different treatment groups. The scale bar represents 10-µm. (n=3 for PBS injected groups, n=8 for AAV9 injected groups, 20 images analyzed/group. *** p<0.001).

Figure 19:
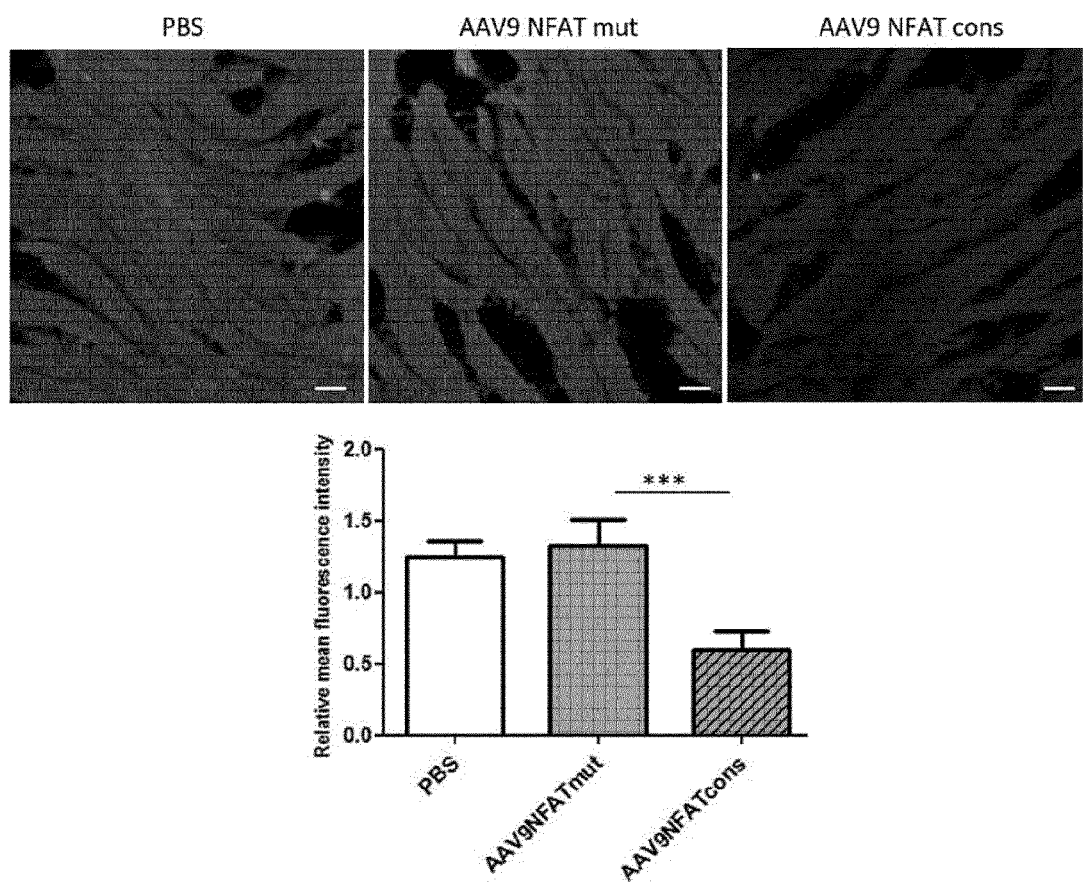

FIG. 19: AAV9-mediated delivery of hpNFAT consensus RNA decoy ODNs decreases the rate of protein translation. Representative images of anti-puromycin immunohistochemistry (red fluorescence) which correlates with the total protein translation rate. The graph depicts the quantification of mean red fluorescence intensity of confocal images in the different treatment groups. Scale bar represents 20 µm. (n=3 for PBS injected groups, n=8 for AAV9 injected groups, 20 images analyzed/group. *** p<0.001).

Figure 20:
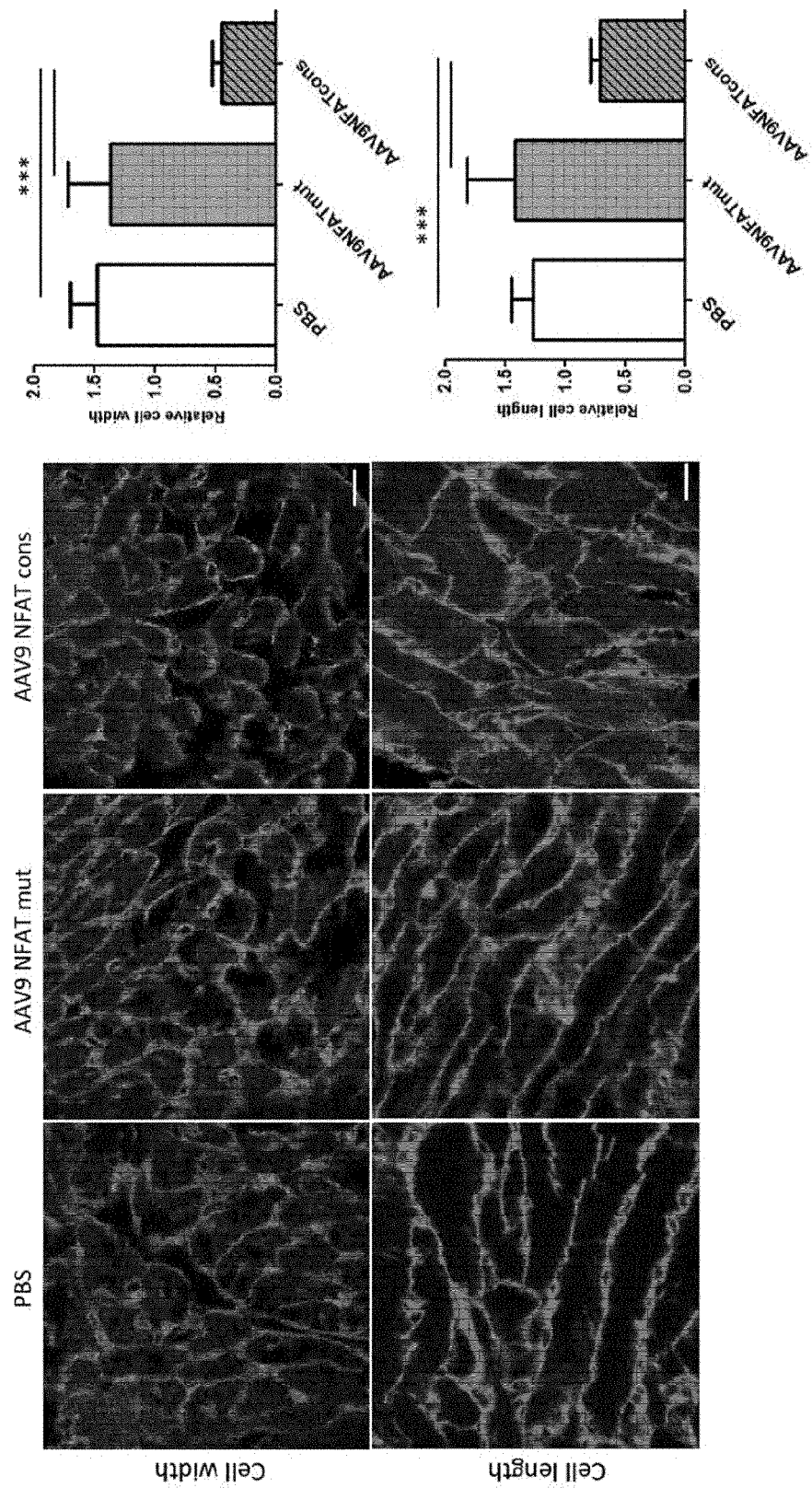

FIG. 20: AAV9-mediated delivery of hpNFAT consensus RNA decoy ODNs decreases cardiomyocyte dimensions. Representative images of wheat germ agglutinin (WGA) stainings (red fluorescence), labeling cell membranes of cells in short and long axis. Cardiomyocyte width and length were analyzed using ImageJ. Scale bar represents 20 µm. (n=3 for PBS injected groups, n=8 for AAV9 injected groups, 20 images analyzed/group, *** p<0.001).

Figure 21:
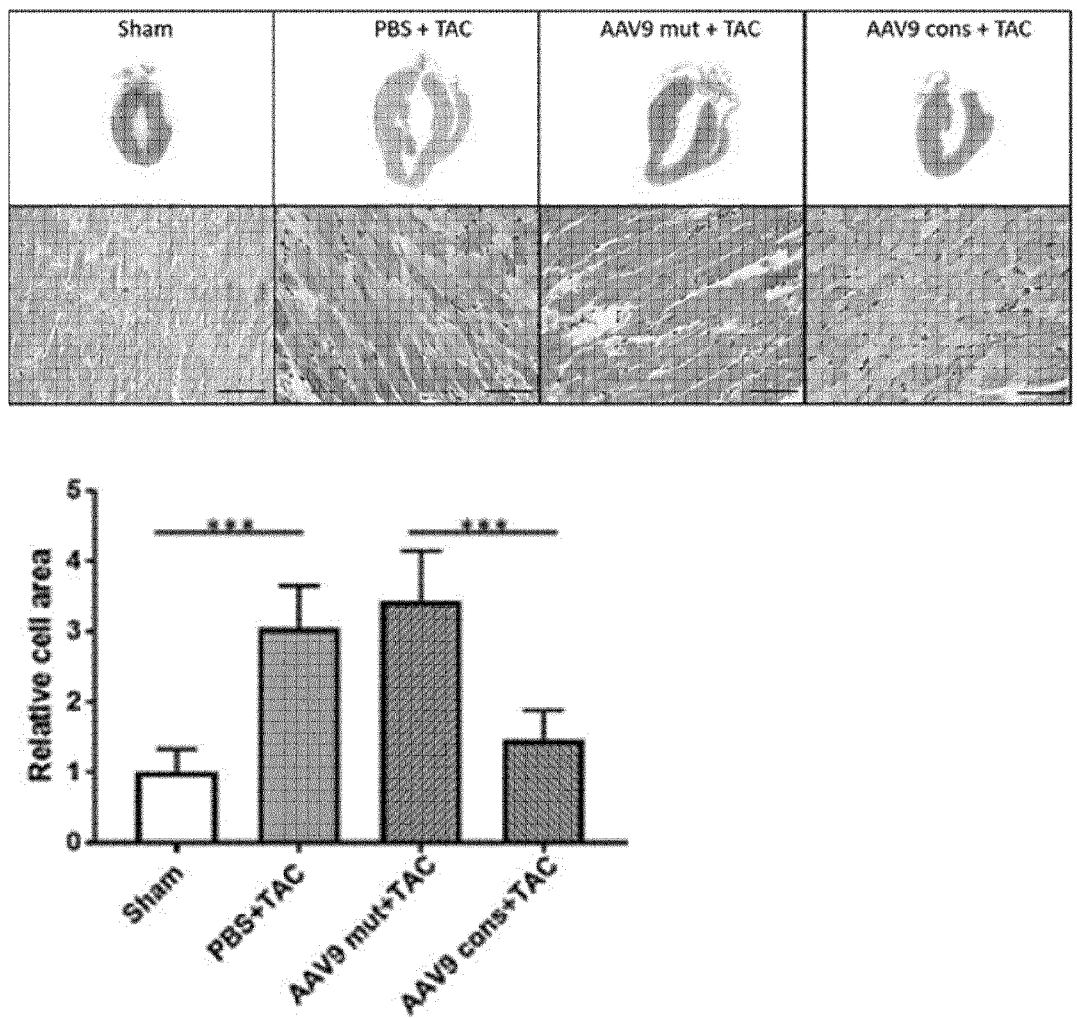

FIG. 21: AAV9-mediated delivery of hpNFAT consensus RNA decoy ODNs reduces left ventricular and cardiomyocyte size. Representative images of hematoxylin-eosin stainings of cardiac tissue sections from mice after TAC as well as from sham operated control animals. The graph shows relative cell area calculated using ImageJ. Values were normalized to the sham group. Scale bar represents 10 µm. (n=3 for PBS injected groups, n=8 for AAV9 injected groups, 15 images analysed/group, *** p<0.001).

Figure 22:
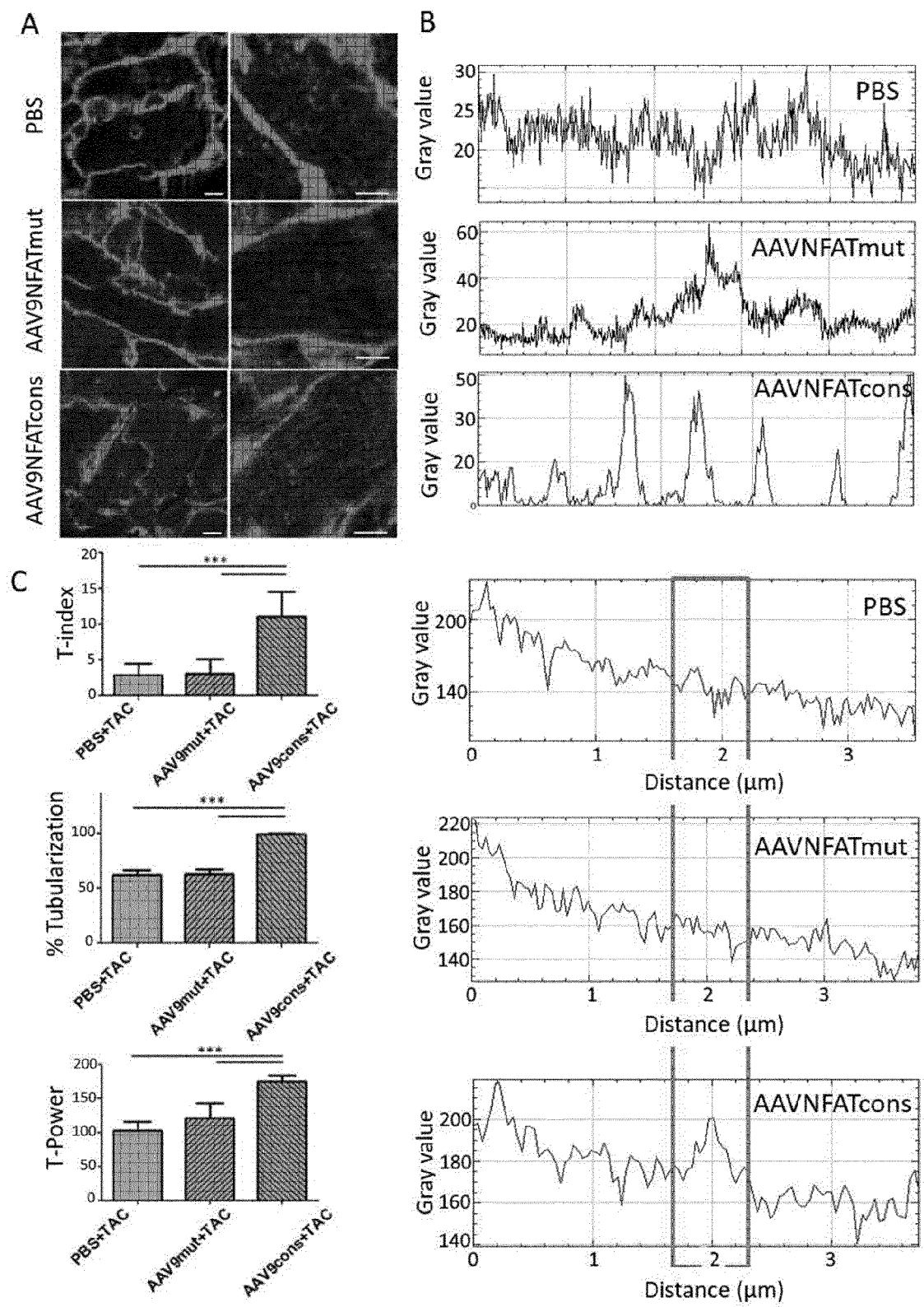

FIG. 22: AAV9-mediated delivery of hpNFAT consensus RNA decoy ODNs improves T-tubule organization in cardiomyocytes. (A) Representative images of WGA stainings (red fluorescence) of myocardium cryosections. Note, that the high red fluorescence background observed in confocal images of the stained tissue next to cell membrane is due to fibrotic areas around cardiomyocytes. (B) Plot profile of WGA stainings showing the regularity of the T-tubule system. (C) Statistical quantification of T-index, percentage of tubulated cells and T-power. The graphs on the right represent the plots obtained after Fourier transformation, showing the frequency of T-tubules at different distances. Scale bar represents 25 µm. (n=3 for PBS injected groups, n=8 for AAV9 injected groups, 30 images were taken/group with different magnifications, *** p<0.001).

Figure 23:
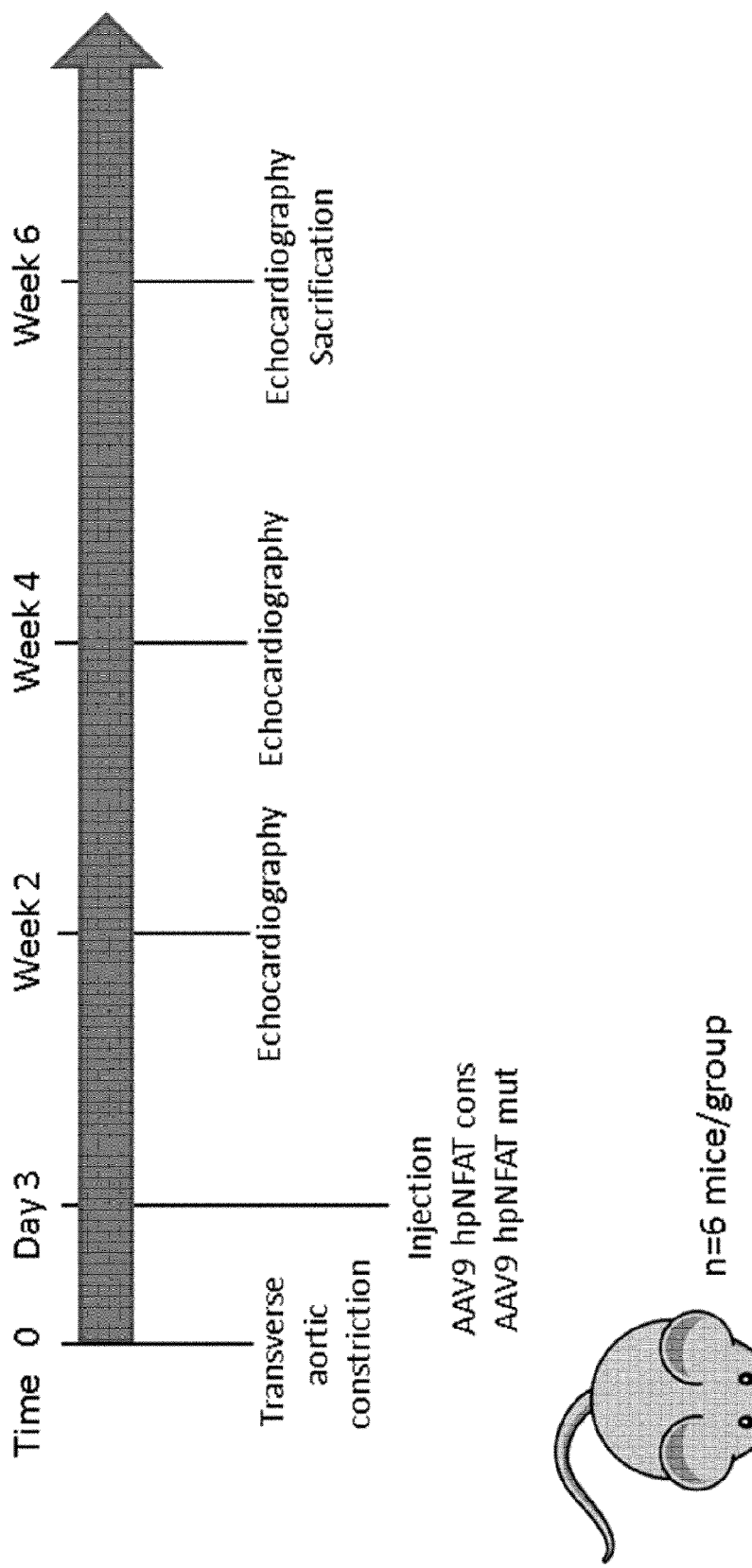

FIG. 23: Scheme of the work flow for the animal proof-of-concept model used (treatment study).

Figure 24:
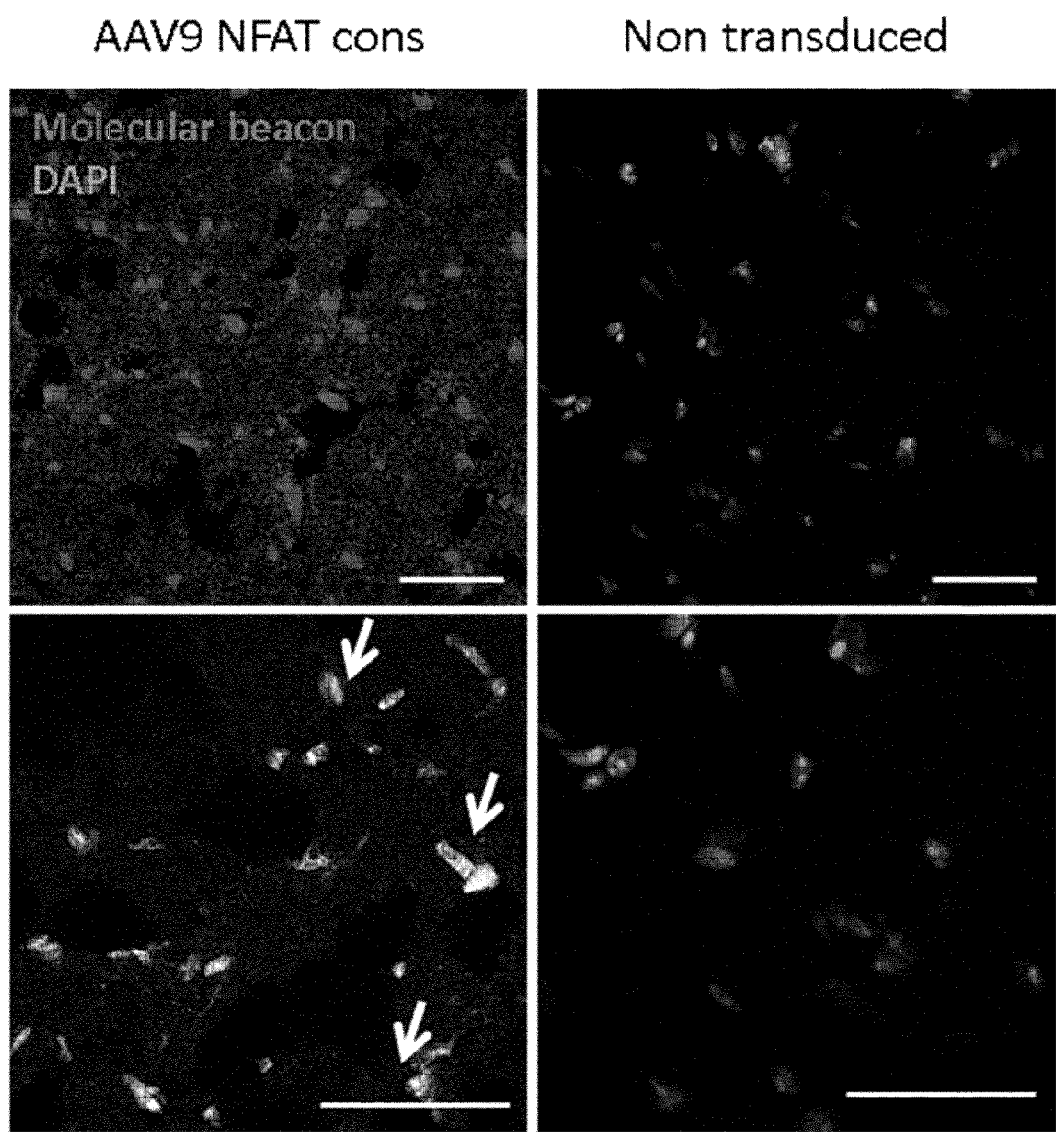

FIG. 24: Detection of the hpNFAT decoy ODNs in the left ventricles of mice subjected to the method of treatment regimen. Representative confocal microscopy images demonstrating the detection of the decoy ODNs (light fluorescence) by fluorescence in situ hybridization (FISH). Nuclei were stained with DAPI (bright fluorescence). Arrows show nuclear localization of the hpNFAT decoy ODNs. Scale bar represents 20 μm.

Figure 25:
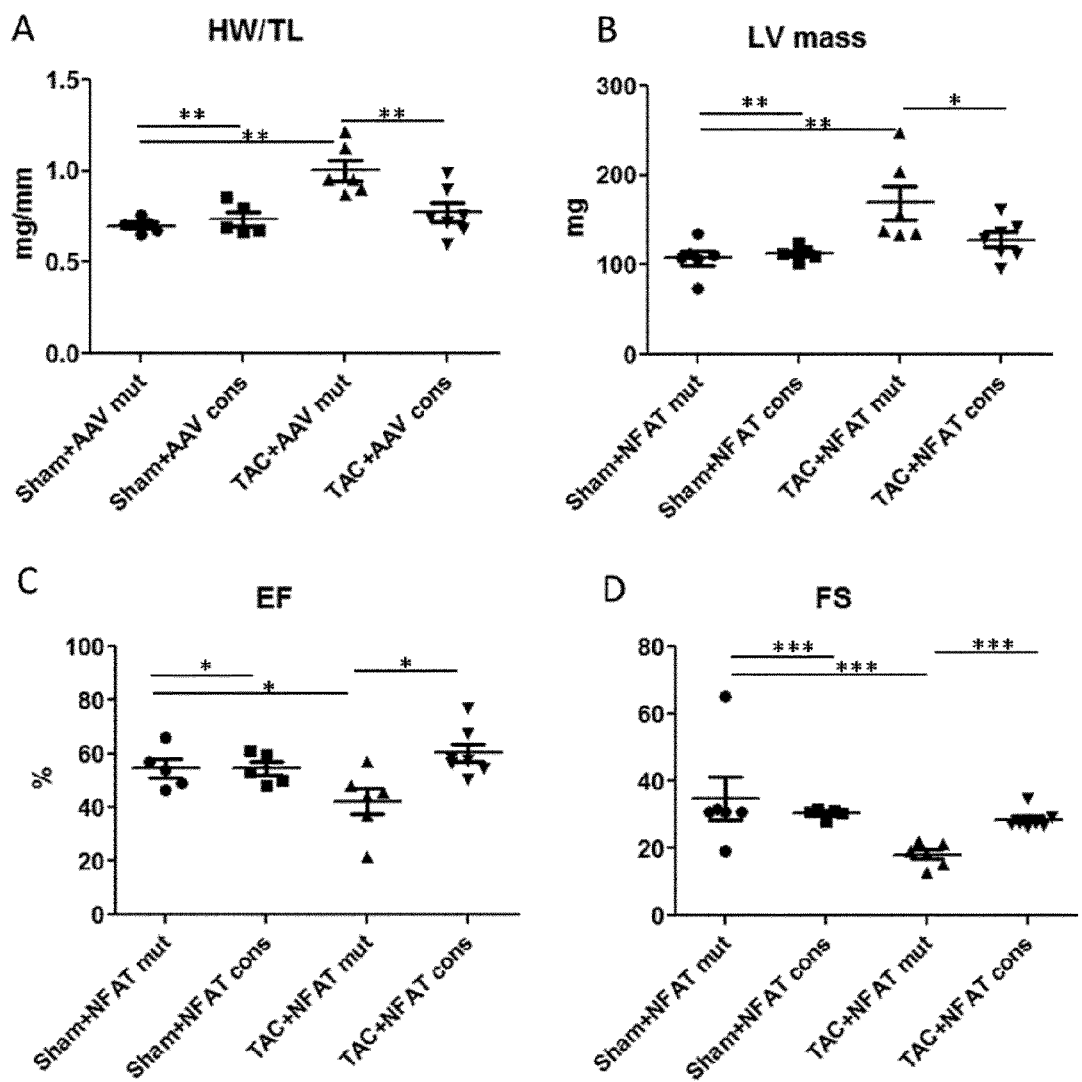

FIG. 25: Reduced hypertrophy and improved heart function following AAV9-mediated hpNFAT consensus RNA decoy ODN delivery into the myocardium 3 days post transverse aortic constriction (TAC). Statistical quantification of hypertrophy markers (A) HW/TL and (B) LV mass, and cardiac functional parameters, measured by echocardiography, (C) ejection fraction (EF) and (D) fractional shortening (FS). LV: left ventricle, HW: heart weight. (n=6 mice/group, *$p<0.05$, $p<0.01$, *$p<0.001$, One-way ANOVA followed by Tukeys multiple comparisons test)

Figure 26:
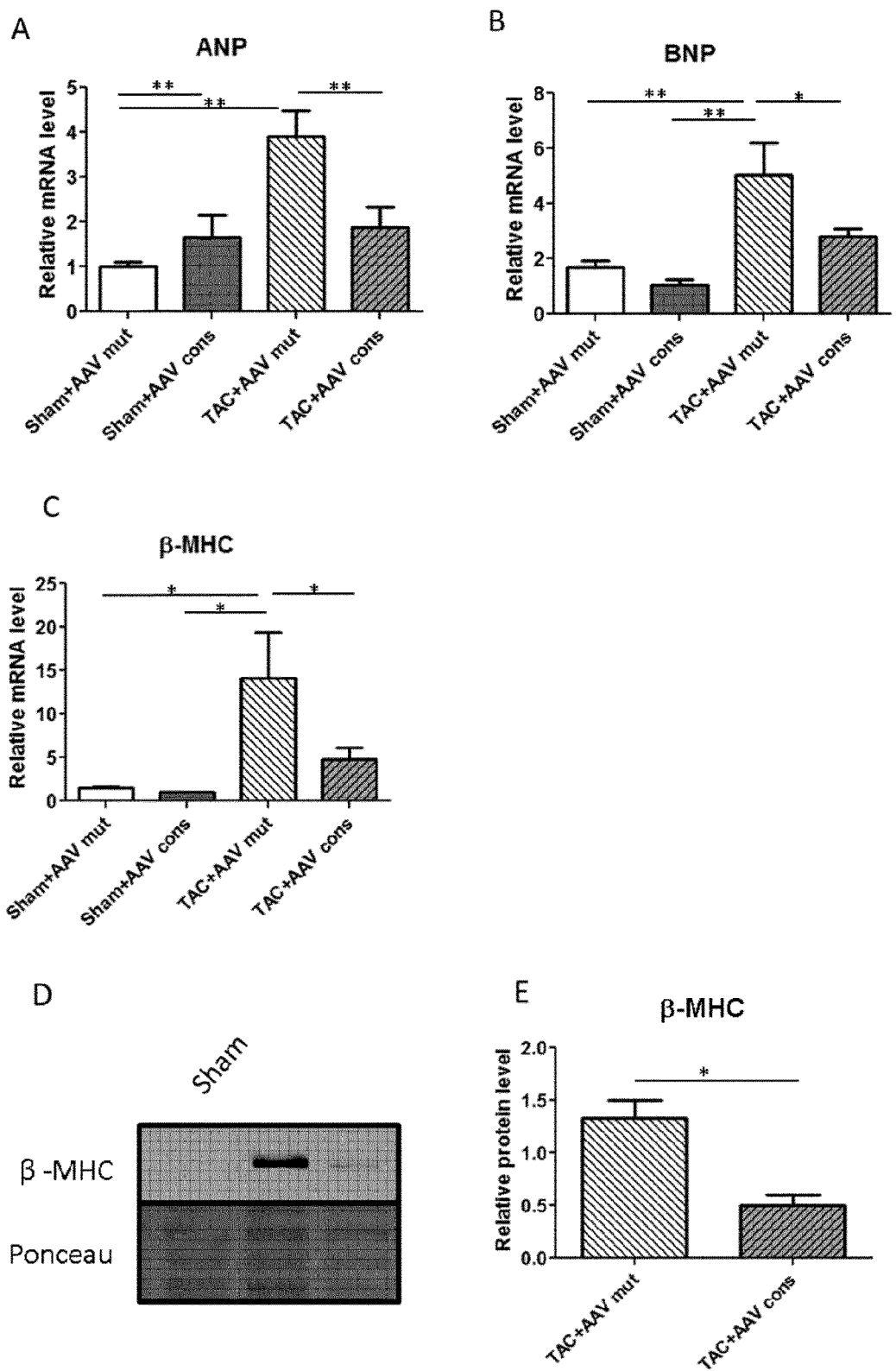
Figure 26:
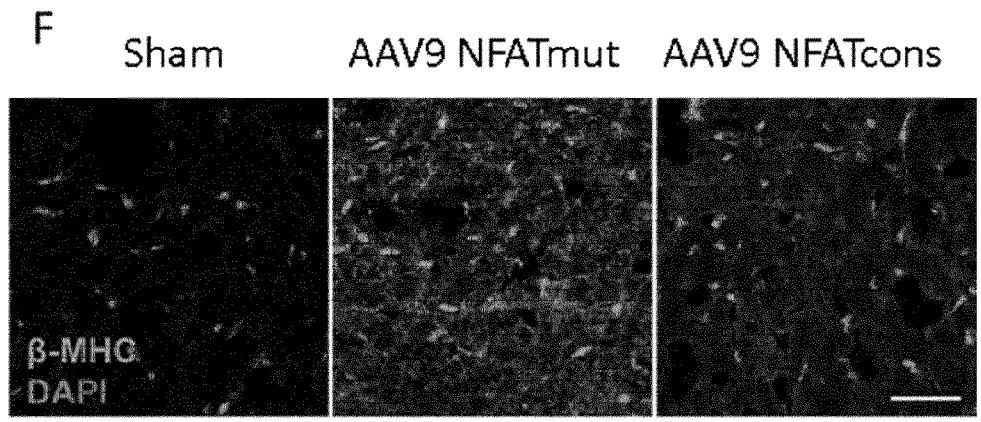

FIG. 26: Reduced fetal gene program following AAV9-mediated hpNFAT consensus RNA decoy ODN delivery into the myocardium 3 days post TAC. Gene expression analysis of (A) ANP, (B) BNP and (C) β-MHC in the left ventricle, using RPL32 as a housekeeping gene. Values were normalized to sham-operated mice as control. (D) Representative image and (E) corresponding quantification of β-MHC protein level in left ventricular whole cell lysates in the mentioned treatment groups. (F) Representative images of β-MHC immunohistochemistry (red fluorescence) in myocardial frozen sections. Nuclei were stained with DAPI (blue). Scale bar represents 20 μm. (n=6 mice/group, *$p<0.05$, **$p<0.01$, One-way ANOVA followed by Tukeys multiple comparisons test)

Figure 27:
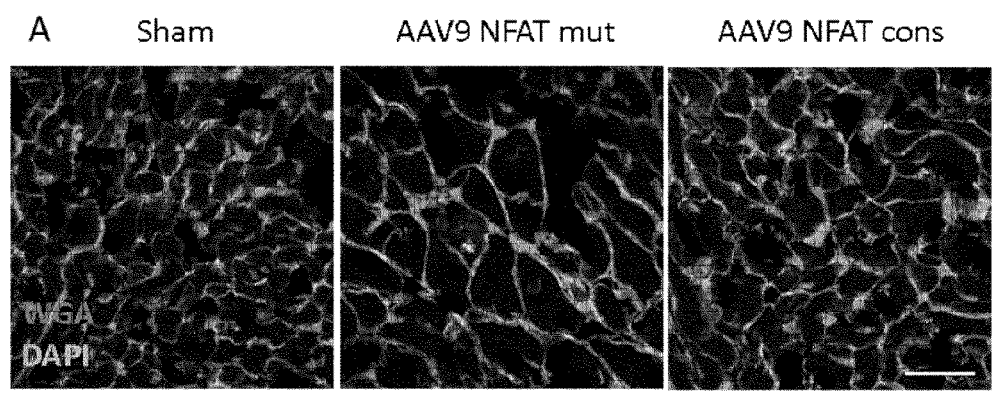
Figure 27:
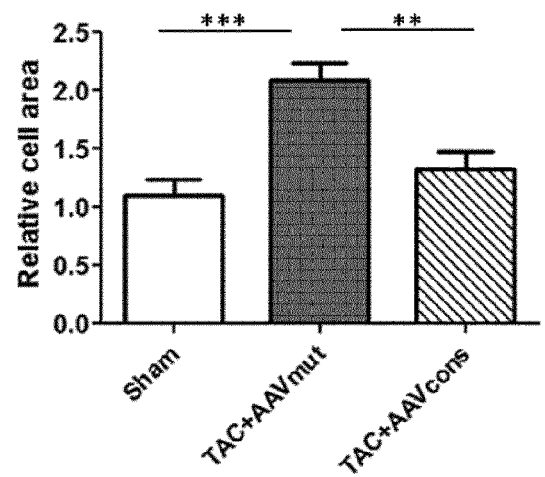

FIG. 27: Decreased cardiomyocyte dimensions following AAV9-mediated hpNFAT consensus RNA decoy ODN delivery into the myocardium 3 days post TAC. Representative images of WGA stainings (magenta), labeling cell membranes of cells in short long axis. Cardiomyocyte cross sectional area was analysed using ImageJ. Scale bar represents 20 μm. (n=6 mice/group, $p<0.01$, *$p<0.001$, One-way ANOVA followed by Tukeys multiple comparisons test)

Figure 28:
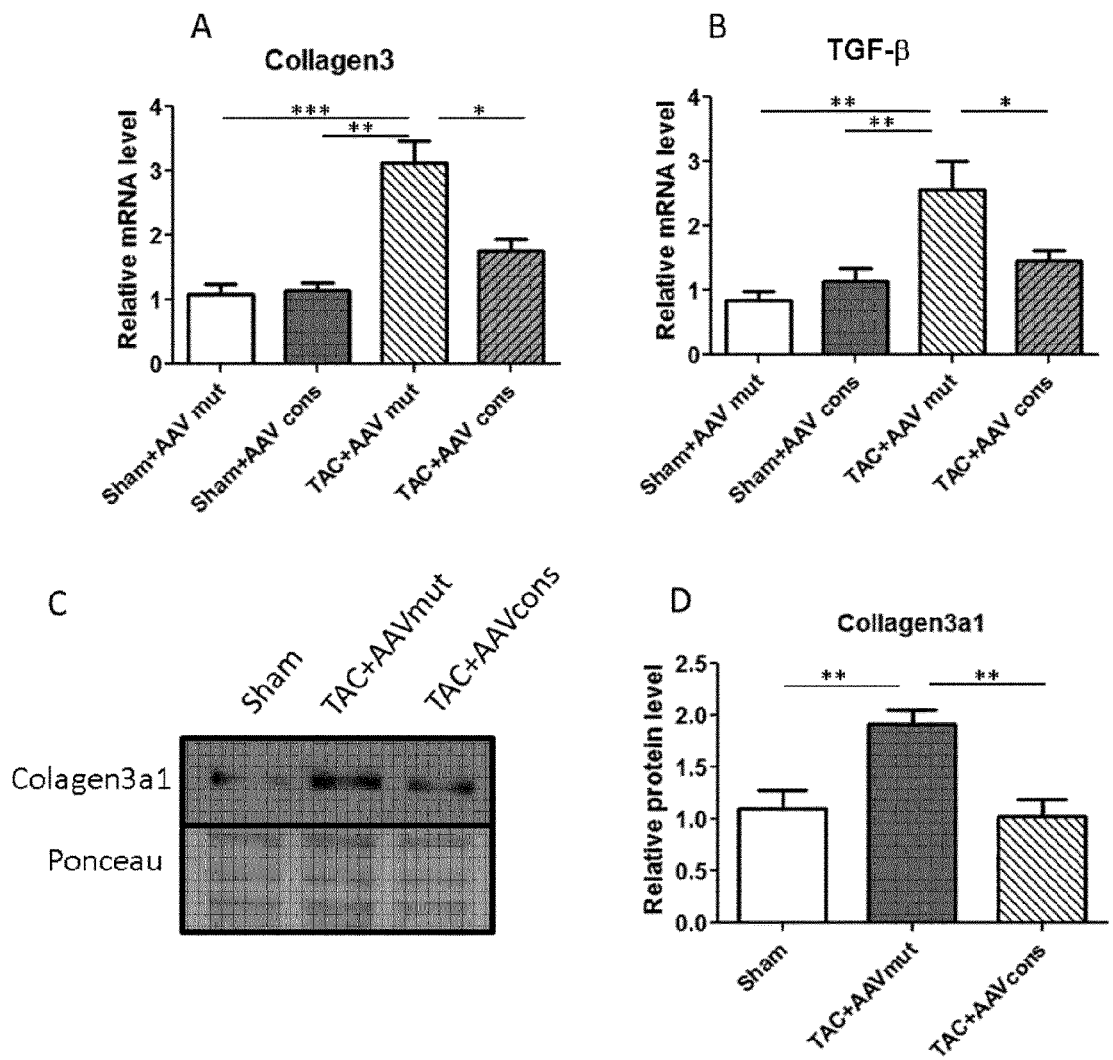

FIG. 28: Decreased fibrosis markers following AAV9-mediated hpNFAT consensus RNA decoy ODN delivery into the myocardium 3 days post TAC. (A, B) mRNA levels of fibrosis markers collagen 3 and TGF-β in cardiac tissue. Gene expression was normalized to RPL32 as a housekeeping gene. (C, D) Western blot analysis of collagen 3a1 protein level in whole cell lysates. (n=6 mice/group, * $p<0.05$, $p<0.01$, *$p<0.001$, One-way ANOVA followed by Tukeys multiple comparisons test)

The following Examples shall merely illustrate the invention. They shall not be construed, whatsoever, to limit the scope of the invention.

Uptake of Naked Hairpin (hp) DNA Decoy ODNs into Cardiomyocytes In Vitro

HL-1 cells (murine cardiomyocyte cell line), neonatal as well as adult murine cardiomyocytes were incubated with the Atto-590 labelled decoy ODNs for 2 hours followed by confocal fluorescence microscopy. This unequivocally revealed uptake of the decoy ODNs into the different cardiomyocytes without any auxiliary means with the Atto-590 fluorescence signal detected both in the nuclei and in the cytoplasm. Transfection with lipofectamine in fact reduced HL-1 cell uptake of the decoy ODNs by approximately 60% (data not shown).

Effects of the Naked DNA-Based hpNFAT Decoy ODNs on Cardiomyocyte Gene Expression and Protein Translation Following serum deprivation HL-1 cells were incubated with the consensus decoy ODN or the mutant control ODN at a concentration of 10 μmol/L for 2 hours followed by exposure to 100 nmol/L endothelin-1 (ET-1), a well-known pro-hypertrophic stimulus for cardiomyocytes, for 24 hours. Exposure to ET-1 resulted in a significant increase in transcription of the fetal genes ANP (atrial natriuretic peptide) and BNP (brain natriuretic peptide) that was virtually abolished by pre-incubation of the HL-1 cells with the consensus decoy ODN but not the mutant control ODN (FIG. 1). The same effect was observed in neonatal murine cardiomyocytes (FIG. 2). Hypertrophic growth of cardiomyocytes is accompanied by an increase in the rate of total protein translation (Hannan R, Jenkins A, Jenkins A, Brandenburger Y (2003) Cardiac hypertrophy: A matter of translation. Clinical and Experimental Pharmacology and Physiology 30: 517-527) that can be determined by employing the non-radioactive SUnSET assay. Pre-treatment of the HL-1 cells with the naked DNA-based consensus hpNFAT decoy ODN but not the mutant control ODN virtually abolished the ET-1-stimulated overall rise in protein translation in the cardiomyocyte cell line (FIG. 3).

Effects of the AAV6-Mediated Expression of RNA-Based hpNFAT Decoy ODNs on Cardiomyocyte Gene Expression and Protein Translation After having demonstrated that the naked DNA-based consensus hpNFAT decoy ODN essentially abolishes the changes in gene expression and protein translation elicited by ET-1 in the cultured cardiomyocytes the next aim was to show that the same effects can be achieved by transducing the cardiomyocytes with an AAV6-based expression vector for expression of a RNA-based consensus hpNFAT decoy ODN. When using these adeno-associated viral vectors at a MOI of $10^5$ viral particles/cell. Using the co-expressed EGFP protein as readout, transduction efficiency for AAV6 in the HL-1 cells was determined to be 80%. Cell viability after transduction was not affected by exposure to AAV6, so that 3 days post transduction, serum-deprived HL-1 cells were stimulated with ET-1 at 100 nmol/L for 24 hours. The resulting increase in fetal gene expression (FIG. 4) and overall protein translation (FIG. 5) was essentially abolished by prior transduction of the HL-1 cells with the RNA-based consensus hpNFAT decoy ODN but not the mutant control ODN.

No Effect of the DNA or RNA-Based Consensus Decoy ODN on NFAT5 Translocation to the Nucleus and NFAT5-Dependent Gene Expression The designed hpNFAT decoy ODN have due to their sequence characteristics a high specificity toward NFAT1 through 4 but should not neutralize NFAT5 because of the different DNA-binding motif recognized by this transcription factor. NFAT5 is a critical transcription factor for the development of the heart and the cellular response to hyperosmotic stress. Consequently, knockout of this transcription factor causes embryonic lethality and for various reasons increased loss of ventricular cardiomyocytes in mice (Mak M C, Lam K M, Chan P K, Lau Y B, Tang W H, Yeung P K K, Ko B C B, Chung S M S, Chung S K (2011) Embryonic lethality in mice lacking the nuclear factor of activated T cells 5 protein due to impaired cardiac development and function. PLOS One 6: 1-8). Therefore, the effects of both the DNA and RNA-based consensus hpNFAT1-4 decoy ODN on hyperosmotic stress-induced nuclear translocation of NFAT5 and NFAT5 target gene expression were investigated in HL-1 cells. As shown in FIG. 6, both decoy ODNs, regardless of the principle of administration, did not affect either parameter in the murine cardiomyocyte cell line, hence proving their specificity for NFAT1-4.

Biological Activity of a cDNA-Based Consensus hpNFAT Decoy ODN In Vitro

In addition, the possibility was explored to express a cDNA-based hpNFAT decoy ODN in the cardiomyocytes and test its biological activity. To this end, an expression vector was designed encoding a viral reverse transcriptase (RT) and the corresponding ODN flanked by a primer binding site. Both sequences are separated by a stem loop structure so that the RT is first transcribed and translated into the active enzyme which then reverse transcribes the other single-stranded RNA template into a single stranded cDNA molecule. The cDNA hybridizes with itself only leaving the hairpin single stranded. The principle of this approach is depicted in FIG. 7 (upper panel).

Subsequently, the expression vector was cloned into a plasmid which was then transfected into HL-1 cells. Successful transfection was verified by the resulting increase in RT activity over baseline in the transfected HL-1 cells (FIG. 7, lower panel). In addition, the molecular beacon technique was used to verify expression of the cDNA-based consensus hpNFAT decoy ODN by the HL-1 cells 2 days post transfection. Both the principle of the molecular beacon technique and the detection of such a single-stranded cDNA-based hairpin decoy ODN is exemplified in FIG. 8 for a bait decoy ODN expressed by HeLa cells. As shown in FIG. 9, plasmid-mediated delivery of the cDNA-based consensus hpNFAT decoy ODN (corresponding to SEQ ID NO:1) but not that of the mutant control ODN to the HL-1 cells nearly abolished ET-1-stimulated fetal gene expression.

Finally, the expression vectors for the consensus and mutant control ODN were cloned into the genome of AAV6 and viral particles produced therefrom. HL-1 cells transduced with these AAVs expressed the cDNA-based decoy ODNs 2 days post transduction as shown by employing the molecular beacon technique (FIG. 10, upper panel). Moreover, only the consensus decoy ODN but not the mutant control ODN expressed by the HL-1 cells virtually abolished the ET-1-stimulated upregulation of ANP and BNP expression in these cells (FIG. 10, lower panel).

Hairpin (hp) NFAT RNA Decoy ODNs Effects In Vivo

In order to prove the in vivo efficiency of the designed AAV, heart hypertrophy was induced by transverse aortic constriction (TAC). AAV9 was previously shown to be the most effective virus serotype to transduce cardiomyocytes in vivo following systemic tail-vein injection (Inagaki K, Fuess S, Storm T A, Gibson G A, Mctiernan C F, Kay M A, Nakai H (2006) Robust systemic transduction with AAV9 vectors in mice: Efficient global cardiac gene transfer superior to that of AAV8. Mol Ther 14: 45-53). Hence, the delivery of hpNFAT RNA decoy ODNs was made by using this virus serotype ($10^{12}$ viral particles/mouse) 2 weeks before surgery, in order to allow the generation of RNA decoy ODNs within the tissue/cardiomyocytes. The survival rate after TAC was 95% (19 surviving mice out of 20). One mouse in the control AAV9 injected group lost a significant amount of weight, developed drastic dilated heart failure with extremely low ejection fraction (20%) and died 5 weeks after surgery.

EGFP and RNA Decoy ODNs Expression after Transduction

Successful cardiomyocyte transduction by AAV9 was demonstrated employing EGFP immunohistochemistry 2 weeks after injection. As shown in FIG. 11A, EGFP protein was detected in the myocardium of both AAV9-injected groups while control PBS treated mice did not present any EGFP signal in cardiomyocytes. These data suggest that cardiomyocyte transduction can be achieved by systemic tail-vein injection of AAV9. The next aim was the detection of hpNFAT RNA decoy ODNs in the cardiomycytes of AAV9 injected animals. Hence, 5-μm heart cryosections were subjected to RNA F.I.S.H. The detection of shRNAs was carried out using a molecular beacon with complementary sequence to the decoy ODNs and which emits red fluorescence when bound to the target. As a control, heart cryosections of PBS-injected mice were used. As presented in FIG. 11B, hpNFAT RNA decoy ODNs were expressed in the tissue isolated from AAV9 injected mice, while samples of PBS treated mice showed no fluorescence signal.

Effect of AAV9 Injection on Heart Function (Prevention Study)

Having determined that AAV9 systemic application leads to cardiomyocyte transduction and subsequently to hpNFAT RNA decoy ODNs production, its effect on heart function was further investigated. A general work flow for the in vivo experiments performed is depicted in FIG. 12. Echocardiography was performed 2 weeks after AAV9 injection to analyze the effect of the designed AAV9 before TAC-induced heart hypertrophy. As shown in FIG. 13, neither AAV9 expressing the consensus hpNFAT nor the mutated RNA decoy ODN had any effect on the ejection fraction at baseline. Consistently, no differences were observed in the calculated LV mass values.

Having established that AAV9 expressing hpNFAT decoy ODNs does not affect heart function at baseline, TAC was performed in AAV9 injected mice and the effect of cell-specific NFAT1-4 neutralization in this heart hypertrophy model was analyzed. Mice were sacrificed 6 weeks after surgery. Since a high variation of body weight was observed between control and TAC-treated groups, the ratio heart weight/tibia length (HW/TL) was used as an established readout for myocardial hypertrophic growth. As shown in FIG. 14A, AAV9 mediated consensus but not mutant hpNFAT RNA decoy ODN expression significantly reduced left ventricular hypertrophy (HW/TL) as compared to the PBS treated group. Moreover, heart failure induced lung edema was analyzed, and the lung weight/TL ratio was in fact dramatically improved following treatment with the consensus decoy ODN expressing AAV9 as compared to vehicle control whereas this parameter tended to be even worse in the mutant control decoy ODN treated group (FIG. 14A). Follow-up echocardiography also revealed prominent amelioration of left ventricular function parameters ejection fraction and left ventricular mass 6 weeks post TAC following NFAT1-4 neutralization by the expressed consensus hpNFAT RNA decoy ODN (FIG. 14B).

Effect of AAV9 Injection on Phospholamban Phosphorylation Status

Phospholamban (PLN) is an important regulator of cardiac contractility by inhibiting SERCA mediated calcium re-uptake into the sarcoplasmic reticulum. Normally, PLN is phosphorylated by protein kinase A (PKA) at serine 16, resulting in an increased calcium sequestration and hence accelerated relaxation of the heart muscle fibers. This so-called lusitropic effect which speeds up ventricular relaxation in diastole is physiologically very important to economize cardiac work during exercise, i.e. at increased heart rate. In pressure overload conditions, such as after TAC surgery, PLN tends to be excessively phosphorylated thus negatively impacting the lusitropic effect. In vehicle control treated mice TAC caused an excessive phosphorylation of PLN at serine 16 (FIG. 15) which was highly significantly inhibited (by 72%) in the TAC group that had been treated with the consensus hpNFAT RNA decoy ODN expressing AAV9 but not with the mutant control decoy ODN expressing AAV9 (FIG. 15).

Effects of AAV9 Injection on the Fetal Gene Program

Next, effects of the AAV9 injection on expression of the pro-hypertrophic markers ANP, BNP and RCAN-1 was examined. As expected, 6 weeks of pressure overload induced a significant increase in expression of these fetal genes in the myocardium as compared to the sham-operated group. Notably, AAV9-mediated expression of the consensus hpNFAT RNA decoy ODN in the cardiomyocytes prior to TAC strongly reduced abundance of these fetal gene products (FIG. 16A). In addition, BNP protein levels were measured in the heart tissue as well as in the plasma from these mice by ELISA. Again, injection of the consensus hpNFAT RNA decoy ODN expressing AAV9 highly strongly reduced both the BNP plasma and tissue level (FIG. 16B).

Effect of AAV9 Injection on Cardiac Fibrosis

Fibrosis is a hallmark of heart failure and associated with collagen deposition contributing to an impairment of cardiac function. It is also known to be part of the TAC-induced cardiac pathology in mice. When analyzed on the mRNA level, the fibrosis markers collagen-3, TGF-β and CTGF were strongly upregulated in the left ventricle of vehicle control treated mice subjected to TAC (FIG. 17A). Treatment with the consensus hpNFAT RNA decoy ODN expressing AAV9 but not the mutant control ODN prior to TAC significantly reduced expression of these markers of fibrosis. It also reduced the rather prominent perivascular and interstitial fibrosis that had developed in the left ventricle of the mice subjected to TAC (FIG. 17B).

Effect of AAV9 Injection on β-MHC Protein Abundance

Heart hypertrophy is characterized by re-activation of the β isoform of the myosin heavy chain, which under normal conditions is expressed in the late stages of embryonic development. Therefore, the relative amount of this protein was analyzed as an additional marker of the pro-hypertrophic response in the 3 different treatment groups of mice subjected to TAC. As shown in FIG. 18, only prior treatment with the consensus hpNFAT RNA decoy ODN expressing AAV9 significantly reduced β-MHC protein abundance by about 50% as compared to both control groups.

Effect of AAV9 Injection on Protein Translation Rate

Cardiomyocyte hypertrophy involves an accelerated protein translation rate which can be determined by using the non-radioactive SUnSET assay. This method was further applied for detection of total protein translation levels in the cardiac tissue of the different treatment groups. Analysis of the confocal images revealed a dramatic decrease in mean fluorescence intensity in the cryosections of mice injected with the consensus hpNFAT RNA decoy ODN expressing AAV9 as compared to both control groups (FIG. 19).

Effect of AAV9 Injection on Cardiomyocyte Size

Next, cardiomyocyte hypertrophy in situ was addressed by directly by measuring cell size. Prior to analysis, cardiomyocyte orientation was analyzed, and both long and short axis were considered for a two-dimensional assessment of cell size. The results obtained (FIG. 20) clearly confirm that AAV9-mediated consensus hpNFAT RNA decoy ODN expression in the left ventricular cardiomyocytes normalizes their size despite subjection of the mice to TAC.

To further confirm these cell size measurements, hematoxilin-eosin staining was performed and relative cardiomyocyte area was analyzed. As expected, TAC induced a significant increase in cell area as compared to sham operated mice (FIG. 21 bottom panel). Moreover, the changes in left ventricular wall dimensions, as assessed by echocardiography were validated by using this technique, resulting in an increased left ventricular wall thickness following TAC (FIG. 21 top panel). Injection of the AAV9 expressing the consensus hpNFAT RNA decoy ODN in the cardiomyocytes two weeks before TAC significantly decreased both left ventricular wall thickness (FIG. 21 top panel) and cardiomyocyte area (FIG. 21 bottom panel) as compared to both control groups.

Effect of AAV9 Injection on T-Tubule Organization

In healthy cardiomyocytes, the T-tubule system is highly organized with a regular spacing distance of approximately 2 μm, which is essential for excitation-contraction coupling. It was previously shown that T-tubule remodeling accompanies the transition from heart hypertrophy to heart failure, namely in animal models of pressure overload. Therefore, it was finally analyzed whether AAV9-mediated neutralization of NFAT1-4 can prevent pathological reorganization of the T-tubules in the TAC model. As expected, TAC led to a dramatic decrease in T-tubule regularity and density in the cardiomyocytes of the left ventricle both in vehicle control and mutant control decoy ODN expressing, AAV9 injected mice (FIG. 22A, B). This effect was almost blunted following pre-treatment with the consensus hpNFAT RNA decoy ODN expressing AAV9. Also T-tubule frequency (T-power), tubularity (T-index) and percentage of tubularization were near normal in the cardiac tissue sections from these mice. These observations allow to conclude that T-tubule network organization and hence excitation-contraction coupling can be rescued by effectively neutralizing NFAT1-4 in the cardiomyocytes of the left ventricle under conditions of pressure overload in mice. They further suggest a beneficial effect of this novel single treatment option on the development of maladaptive heart hypertrophy as well as its transition to heart failure in vivo.

Effect of AAV9 Injection on Heart Function (Treatment Study)

To investigate whether AAV9-mediated delivery of the hpNFAT consensus RNA decoy ODN into the myocardium can alleviate cardiac hypertrophy after transverse aortic constriction (TAC), the vector ($10^{12}$ virus particles/mouse) was injected systemically through the tail vein 3 days after surgery. Heart function was monitored in a blinded manner every 2 weeks by echocardiography. Mice were sacrificed 6 weeks after TAC (FIG. 23).

Hairpin NFAT Consensus Decoy ODNs are Expressed after AAV9 Tail-Vein Injection

To prove that the hpNFAT consensus RNA decoy ODN is expressed following AAV9 transduction, we subjected myocardial frozen sections to FISH. As a probe, we used a molecular beacon with complementary sequence to the decoy ODN, which emits red fluoresce following hybridization to its target. As shown in FIG. 24, successful generation of the active nucleic acid compound was detected in AAV9-transduced myocardial tissue, whereas in non-transduced control myocardial sections no fluorescence could be detected. Importantly, this method confirmed presence of the hpNFAT decoy ODNs in the nucleus, which is a key factor for exerting their activity.

Decreased Hypertrophy and Improved Cardiac Function Following AAV9-Mediated hpNFAT Consensus RNA Decoy ODN Expression in the Myocardium 3 Days Post TAC Administration of hpNFAT consensus (cons) but not mutant control (mut) RNA decoy ODN-expressing AAV9 viral vectors to mice subjected to TAC 3 days before strongly ameliorated myocardial hypertrophy, as shown by the decreased HW/TL ratio and LV mass (FIG. 25A, B). Moreover, echocardiographic analysis revealed a marked improvement in cardiac function, as evidenced by normalization of both ejection fraction and fractional shortening (FIG. 25C, D). Mice treated with the mutant control RNA decoy ODN-expressing viral vectors presented with prominent cardiac hypertrophy and pronounced deterioration of myocardial function as compared to the sham group.

No Switching on of the Pro-Hypertrophic Gene Program Following Following AAV9-mediated hpNFAT consensus RNA decoy ODN expression in the myocardium 3 days Post TAC The effects of AAV9-mediated hpNFAT decoy ODN delivery to the cardiomyocytes in vivo was further evaluated with respect to TAC-mediated activation of the fetal gene program. Pressure-overload induced hypertrophy caused a significant rise in mRNA levels of atrial natriuretic peptide (ANP, 3.9-fold increase), brain natriuretic peptide (BNP, 5-fold increase) and the β-isoform of myosin heavy chain (β-MHC, 14-fold increase) in mice injected with the hpN-FAT mut RNA decoy ODN-expressing AAV9 as compared to sham treated mice (FIG. 26 A-C). Furthermore, β-MHC protein level was elevated in left ventricles of these mice (FIG. 26 D-F). In stark contrast, administration of the hpNFAT cons RNA decoy ODN-expressing viral vectors 3 days after TAC led to normalization of all marker gene products for the hypertrophic cardiomyocyte phenotype, validating the rapid, prominent and long-lasting positive effect of this one-time treatment.

Decreased Cardiomyocyte Hypertrophy Following AAV9-Mediated hpNFAT Consensus RNA Decoy ODN Expression 3 Days Post TAC Next, cardiomyocyte cross-sectional areas in the different treatment groups was assessed by specific staining of the cell membrane using WGA. Analysis of confocal fluorescence microscopy images demonstrated substantial cardiomyocyte hypertrophy 6 weeks following TAC in the mutant control RNA decoy ODN-treated control group as compared to sham-treated mice (2-fold increase in cross sectional area, FIG. 27A, B). Conversely, expression of the hpNFAT consensus RNA decoy ODN exerted a profound anti-hypertrophic effect, as evidenced by a dramatic reduction in cross-sectional area almost back to the level of the sham-treated control mice (FIG. 27A, B).

Evidence for Decreased Fibrosis in Mice Treated with the hpNFAT Consensus RNA Decoy ODN-Expressing AAV9 Vectors Considering that cardiac fibrosis is a hallmark of heart failure and cardiac dysfunction, this parameter was investigated in addition to the above. As shown in FIGS. 28A and B, gene expression analyses revealed a significant decline in collagen 3 and TGF-β mRNA levels in the heart of mice subjected to TAC and treated 3 days later with the hpNFAT consensus RNA decoy ODN-expressing viral vector (1.8-fold and 1.7-fold, respectively) as compared to mice treated with the hpNAFAT mutant control decoy ODN-expressing AAV9. Consistently, Western Blot analysis confirmed a 1.8-fold reduction (i.e. back to the level of the sham-treated control mice) in collagen 3 protein content in the myocardium of mice therapeutically treated with the hpNFAT consensus RNA decoy ODN-expressing viral vector (FIG. 28C, D).

In conclusion, continuous expression of a hairpin RNA decoy ODN neutralizing the transcriptional activity of NFAT in cardiomyocytes in vivo not only effectively prevents TAC-induced cardiac hypertrophy transiting into heart failure in mice but when administered therapeutically, i.e. 3 days post TAC, almost completely normalizes cardiac structure and function on several levels in this animal model. Both proof-of-concept studies thus suggest that one-time treatment with a viral vector specifically targeting cardiomyocytes in which a NFAT-neutralizing hairpin RNA decoy ODN is subsequently expressed may not only ameliorate the symptoms of cardiac hypertrophy in humans but also prevent the transition of cardiac hypertrophy into heart failure. Hairpin RNA-based decoy ODNs are not only much more effective than double-stranded DNA-based decoy ODNs but offer the opportunity to express them directly in their target cells, here cardiomyocytes, rather than to topically administer them, which is in fact impossible with an internal organ such as the heart. AAVs offer the opportunity to specifically target cells in the body despite a systemic route of application and in addition provide long-term expression of their cargo vector in the target cells. Only the combination of cargo and vector plus the specificity of the decoy ODN for the target transcription factor therefore makes a one-time treatment option for the treatment of, e.g. cardiac diseases, feasible.

The following section describes the methods used to conduct the afore-mentioned in vivo study.

AAV Production

AAV production was performed in collaboration with Prof. Oliver Müller, Dr. Andreas Jungmann, Clinic for Cardiology, Angiology and Pneumology, University Clinic Heidelberg according to standard protocols (Varadi K, Michelfelder S, Korff T, Hecker M, Trepel M, Katus H, Kleinschmidt J, Müller O J (2012) Novel random peptide libraries displayed on AAV serotype 9 for selection of endothelial cell-directed gene transfer vectors. Gene Therapy 19:800-809).

Cloning of hpRNA Decoy ODNs Expressing Plasmids

The hpRNA decoy ODNs were generated as shRNAs under the H1 promoter. The plasmids encoded EGFP as an expression marker under the control of a CMV promoter, and included inverted terminal repeats (ITR) sequences, which are crucial for AAV production. The individual sequences for each shRNA subcloning were ordered as gene synthesis (see table below). The synthetized gene sequences contained part of the H1 promoter (5'-end) and the shRNA (3'-end) flanked by KasI and XhoI restriction sites.

TABLE

List of gene synthesis sequences.
Sequences recognized by restriction
enzymes are presented in italic and
decoy ODN sequences are shown in bold.

| Plasmid | Sequence |
| --- | --- |
| P-NFAT cons (SEQ ID NO: 18) | 5'AGGCGCCCTGCAATATTTGCATGTCG CTATGTGTTCTGGGAAATCACCATAAAC GTGAAATGTCTTTGGATTTGGGAATCTT ATAAGTTCTGTATGAGACCACAGTCGAC GAGTGGAAACATACAGCCACTGAAACAG TGGCTGTATGTTTCCACTCCACCGCAGT TTCGAC*CTCGAGA*3' |
| P-NFAT mut (SEQ ID NO: 19) | 5'AGGCGCCCTGCAATATTTGCATGTCG CTATGTGTTCTGGGAAATCACCATAAAC GTGAAATGTCTTTGGATTTGGGAATCTT ATAAGTTCTGTATGAGACCACAGTCGAC GAGCTTAAACATACAGCCACTGAAACAG TGGCTGTATGTTTCCACTCCACCGCAGT TTCGAC*CTCGAGA*3' |

Maintainence of Bacterial Cells

For AAV plasmid cloning, recombination-deficient SURE2 (Stop Unwanted Rearrangement Events 2) bacterial cells (Agilent Genomics, Waldbronn, Germany) were used, in order to prevent the deletion of ITR sequences. Liquid cultures, grown in sterile LB medium were expanded at 37° C. under continuous agitation (150-200 rpm) in a bacterial incubator. Bacteria stocks for transformation were stored as 50 µL aliquotes at −80° C.

Digestion of Plasmid DNA

Plasmid digestion with KasI and XhoI restriction enzymes was performed in the corresponding buffers for 2 h for each µg plasmid DNA, at 37° C. Reaction efficiency was analyzed by agarose gel electrophoresis (100V for approximately 70 min). A molecular weight ladder was used to determine band size (GeneRuler 1 kb DNA Ladder, Thermo Fischer Scientific, Munich, Germany). The DNA was imaged by using a GelDoc XR unit and analyzed using the Quantity One software package version 4.06 (Bio Rad, Munich, Germany). The DNA bands corresponding to the backbone and the insert were cut out and DNA was purified from the gel using QIAquick Gel Extraction Kit (Qiagen, Hilden, Germany) according to the manufacturer's instructions. Eluted DNA concentration was measured using NanoDrop spectrophotometer (PeQlab Biotechnologie, Erlangen, Germany).

Modification of DNA Ends

In order to reduce the process of backbone re-ligation, 5'-phosphate ends were removed by using Antarctic phosphatase (New England Biolabs, Frankfurt am Main, Germany). The gel-purified vector backbone was incubated with the enzyme in the specific buffer for 30 min at 37° C. Phosphatase heat-inactivation was afterwards performed at 65° C. for 30 min on a thermoblock (Eppendorf, Hamburg, Germany).

Ligation of Plasmid DNA

Ligation of DNA fragments was performed in a ratio of 1:4 backbone:insert by using T4 DNA ligase in the specific ATP-containing buffer provided by the producer. For each ligation reaction, 50 µg backbone was used. The dephosphorylated backbone was incubated with the insert in the presence of ligase for 16 hours at 16° C. using a thermoblock. The reaction mixture was further used for transformation of the bacteria.

Bacterial Transformation

Fifty µL of bacteria were allowed to thaw on ice and then incubated with the ligation mixture for 30 min at 4° C. Heat-shock was performed at 42° C. for 45 s, on a thermoblock. Afterwards, bacteria were transferred on ice for 10 min and then cultured for 30 min at 37° C. in 300 µL LB medium without antibiotics. Next, the suspension was spread on sterile LB-plates with 15% agar and 100 µg/mL ampicillin (Sigma-Aldrich, Munich, Germany). Plates were incubated overnight at 37° C. to allow colony formation. Individual bacterial colonies were randomly picked and further cultured in 5 mL LB medium with ampicillin for 16 hours. Plasmid DNA was isolated using the QIAprep Spin Miniprep Kit (Qiagen, Hilden, Germany) according to the manufacturer's instructions.

The presence of the insert was confirmed by KasI and XhoI digestion as well as DNA sequencing (Eurofins Genomic, Luxembourg). Positive colonies were expanded in 1 L of ampicillin containing LB medium overnight and DNA was isolated using the ZymoPURE Plasmid Gigaprep Kit (Zymo Research, Freiburg, Germany) according to the manufacturer's instructions. Each preparation yielded at least 1.5 g plasmid DNA, which was further used for AAV preparation.

Quantitative Real Time PCR Total RNA was extracted from cardiac tissue using the RNeasy Mini Kit (Qiagen, Hilden, Germany) following the manufacturer's instructions and RNA concentration was measured using a NanoDrop spectrophotometer (PeQlab Biotechnologie, Erlangen, Germany). First strand synthesis of cDNA was completed using Omniscript Reverse Transcriptase kit (Qiagen) and OligodT primers (Promega, Mannheim, Germany), starting from equal amounts of RNA for each sample. SYBR Green (Qiagen) qRT-PCR was performed using the Qiagen Rotor-Gene cycler in reactions of 20 µL (10 µL SYBR Green, 2 µL primer mix, 3 µL RNase free water, 5 µL cDNA). cDNA was amplified using specific primers for the genes of interest. The qPCR program consisted of an initial denaturation step of at 95° C. for 5 min followed by 40 cycles of denaturation (at 95° C. for 60 s), annealing (primer dependent temperature, 25 s) and elongation (72° C. for 60 s) followed by monitoring of the melting curve. The presence of a single amplicon was determined by the existence of a single peak in the melting curve graph. Data was analyzed by relative quantification using the double delta Ct (cycle threshold) method with RPL32 as a housekeeping gene (Pfaff M W (2001) A new mathematical model for relative quantification in real-time RT PCR. Nucleic Acids Res 29: 2003-2007). The Ct was defined as the cycle number at which the fluorescence signal crosses the fluorescence threshold, considered as background. Corresponding controls (samples isolated from control mice) were used for relative gene expression calculation.

In Situ Hybridization

For the detection of RNA decoy ODNs ex vivo, samples (tissue sections) were subjected to RNA in situ hybridization. In brief, 5-µm tissue cryosections were fixed with DEPC (diethyl dicarbonate)-treated 4% p-formaldehyde (Sigma-Aldrich, Munich, Germany) for 10 min followed by incubation with 20 µg/mL proteinase K (Sigma-Aldrich, Munich, Germany) at 37° C. for 15 min in order to induce tissue permeabilization and antigen retrieval. As a probe, a molecular beacon (Biomers, Ulm) with complementary sequence to the hairpin decoy ODNs with 5'-Cy5 labeling and 3'-BHQ-2 (Black Hole Quencher) as a quencher was employed. In the hybridized state, the molecular beacon itself does not emit a fluorescence signal due to the dye and the quencher being located proximal to each other. After hybridization to the target sequence, red fluorescence can be detected (Wile B M, Ban K, Yoon Y S, Bao G (2014) Molecular beacon-enabled purification of living cells by targeting cell type-specific mRNAs. Nature Protocols 9: 2411-2424). Prior to hybridization, the molecular beacon was heated to 95° C. followed by gradual cool-down to ambient temperature to allow the hairpin structure to form; afterwards it was kept on ice until use.

The molecular beacon technique was also used to detect the expressed and reversed transcribed cDNA-based consensus and control hpNFAT decoy ODNs, e.g. in HL-1 cells. Other than described above the molecular beacons were labeled with 6-carboxyfluorescein (6-FAM) at the 5' end and with BHQ-1 at the 3' end. They were incubated with the plasmid transfected HL-1 cells 2 days post transfection as described below followed by fixation of the HL-1 cells, counterstaining with DAPI and fluorescence microscopy analysis.

Samples were incubated overnight at 55° C. with the probe dissolved in hybridization buffer in a humidified atmosphere. As blocking reagents, salmon DNA and yeast tRNA were added to the mixture. After extensive washes (3×20 min) in hybridization buffer and DEPC-treated PBS (lx 15 min) to remove non-hybridized molecular beacon, EGFP immunofluorescence staining was performed. Finally, DAPI staining was performed (excitation at 358 nm/emission at 461 nm) for visualization of the nuclei using Fluoroshield with DAPI mounting medium (Sigma-Aldrich).

Protein Extraction and Western Blot Analysis

In order to isolate total protein from cardiac tissue, a piece of the left ventricle was cut, briefly washed with NaCl to remove blood residuals, and then treated with 300 μL complete RIPA buffer at 0-4° C. Afterwards, a Dounce homogenizer was used to disrupt the tissue. Protein lysates were snap frozen and maintained at −80° C. before further analysis. To this end, 30 μg of protein were denatured by incubation at 95° C. for 10 min with 4× sample buffer (Roth, Karlsrue, Germany) and loaded onto 12% polyacrylamide gels with SDS. A pre-stained protein standard (Bio Rad, Munich, Germany) was used for molecular weight estimation. Separated proteins were transferred onto a methanol pre-activated PVDF (polyvinylidene difluoride) membrane (Merck Millipore, Darmstadt, Germany) with a pore size of 0.45 μm. Ponceau S (Roth, Karlsrue, Germany) staining was used to document equal loading of protein samples. The membranes were then digitized using a Lexmark scanner. Prior to further processing, the membranes were completely destained by washing with TBS.

Blocking was made using 5% nonfat dry milk diluted in TBS-T for one hour, followed by overnight incubation at 4° C. under continuous shaking with the primary antibodies; 3-actin was used as a loading control. After washing, membranes were incubated with the corresponding horseradish-peroxidase labeled secondary antibodies for 1 hour at ambient temperature. Membranes were developed with the chemoluminescent substrates Luminata Classico (Merck, Darmstadt) for β-actin and Luminata Forte (Merck) for phospholamban detection for 3 min. Afterwards, membranes were imaged using the ImageQuant LAS 4000 mini system (GE Healthcare Life Sciences, Munich, Germany). The band intensities were analyzed and related to β-actin using ImageJ software.

ELISA

ELISA (enzyme-linked immunosorbent assay) was used for the assessment of BNP concentration in left ventricular protein extracts and in plasma. For this purpose, a Brain Natriuretic Peptide EIA Kit (Sigma-Aldrich) was used according to the manufacturer's instructions. The absorbance was read using a colorimetric microtiter plate reader (BioTek, Bad Friedrichshall, Germany). Absorbance of the samples and standards was measured in duplicate. A standard curve for the target protein (provided by the manufacturer) was plotted in each experiment. The amount of BNP protein was normalized to the total protein content of the sample, as determined by using the Bradford method.

Immunohistochemistry

Cardiac tissue was collected and washed in NaCl to remove blood residuals. Next, tissue was embedded into TissueTek (Leica Biosystems, Wetzlar, Germany) and snap-frozen by immersion into liquid nitrogen. A cryotome (Leica, Mannheim, Germany) was used to section the frozen tissue (temperature −21° C.) into 5-μm thick cryosections that were fixed with Zinc fixative and blocked with PBS containing 3% BSA and 0.05% Triton-X100 for 1 hour. Primary antibodies against the proteins of interest were diluted in blocking buffer and incubated overnight at 4° C. in a humidified atmosphere. As secondary antibodies, compatible Cy3 or Cy5 labeled IgGs were used, diluted in blocking buffer. Nuclei were visualized by DAPI counterstaining and images were recorded by confocal microscopy (Leica TCS SP8, Leica Microsystems, Mannheim). Relative mean fluorescence intensity was measured using ImageJ as previously described (Jensen E C (2013) Quantitative analysis of histological staining and fluorescence using ImageJ. The Anatomical Record 296: 378-381) and related to the corresponding controls.

SUnSET Assay

The SUnSET (surface sensing of translation) assay was used for measurement of total protein translation rate as previously described (Schmidt E K, Clavarino G, Ceppi M, Pierre P (2009) SUnSET, a nonradioactive method to monitor protein synthesis. Nature Methods 6: 275-277). To this end, 5-μm cardiac cryosections were incubated with 10 μmol/L puromycin for 30 min followed by fixation with p-formaldehyde. Then the anti-puromycin antibody diluted in blocking buffer was added to fixed sections and incubated overnight at 4° C. After 3 steps of washing with PBS, a Cy5-labeled secondary antibody was incubated with the tissue sections followed by monitoring of the ensuing red fluorescence signal using the confocal microscope and analysis of relative mean values using ImageJ software.

Cell Size Measurement

WGA (Wheat Germ Agglutinin) staining is an already established method for analysis of cell size in cardiac tissue. Left ventricles embedded in TissueTek medium were sectioned (5 μm) and the cell orientation was observed. The analysis was made on both short and long axis. Cryosections were fixed with PFA 4% for 5 min and stained with WGA-Alexa Fluor 594 (Thermo Fischer Scientific, Darmstadt, Germany, 1:400 diluted in PBS). The incubation with the dye was performed at room temperature, for 10 min. Afterwards, tissues were briefly washed with PBS and mounted. Images were taken using confocal microscopy and cell diameter was analyzed using ImageJ.

T-Tubule Analysis

After wheat germ agglutinin staining, T-tubule organization was assessed using ImageJ, as previously described (Wei S, Guo A, Chen B, Kutschke W, Xie Y P, Zimmerman K, Weiss R M, Anderson M E, Cheng H, Song L S (2010) T-tubule remodeling during transition from hypertrophy to heart failure. Novelty and significance. Circulation Research 107:520-531). In brief, cardiomyocytes in the tissue sections were analyzed individually by application of fast Fourier transformation (FFT). This method allowed the identification of repetitive patterns and the frequency with which they appear (T-power). The peak corresponding to the 2-μm distance was further analyzed. In addition, the percentage of cell area occupied by T-tubules (T-index) was calculated by using threshold method deter-mined in ImageJ. This parameter was defined as the area above-threshold divided by cell cross-sectional area. Cardiomyocytes presenting with a T-index above 2% were considered to be tubulated. The level of tubularization was defined as the percentage of tubulated cells in each treatment group.

Masson's Trichrome Staining

Hearts were fixed in 4% p-formaldehyde overnight at 4° C. and embedded in paraffin prior to histological assessment. For visualization of collagen fibers, sections were subjected to Masson's Trichrome staining according to standard protocols. Images were taken in random areas of the left ventricle using a brightfield microscope with 20× magnification (Leica DM500, Leica Microsystems, Mannheim, Germany). Collagen was stained blue, muscle and cytoplasm appeared red and nuclei were visualized as being dark brown to black. Both perivascular and interstitial fibrosis were analyzed using a quantification software written in QT/C++ based on image processing and segmentation libraries. In a first step, interfering background of all images was masked out by subsequently applying threshold and erosion filters. Further, the fibrotic area was determined using hsv-thresholding with a 10% tolerance on the hue component, followed by numerical quantification of the percentage area covered.

Hematoxylin-Eosin Staining

Cardiomyocyte architecture was assessed by hematoxylin-eosin staining of paraffin-embedded tissue sections according to standard protocols. Stained tissue sections were visualized using a brightfield microscope (Leica DM500, Leica Microsystems). Following the procedure, nuclei appeared blue, while cardiac tissue was stained pink. Cardiomyocytes were identified according to their specific shape and their area on the long axis was measured using ImageJ and normalized to the cell size of sham operated mice.

Animal Model

All animal experiments were carried out under the approval of the regional animal ethics committee (Regierungspräsidium Karlsruhe, permit number G180/12, and Ministry of Environmental and Agricultural Affairs of Schleswig-Holstein, permit number V312-7224.121-4); applicant Prof. Dr. Oliver Müller). Animals were kept in the Interfaculty Biomedical Facility (IBF), Heidelberg or the Zentrale Tierhaltung, Universitätsklinikum Schleswig-Holstein, Campus Kiel, under standard conditions with 12-hour light and 12-hour night cycle; water and food was offered ad libitum.

Transverse Aortic Constriction and Echocardiography

Transverse aortic constriction was performed in 10 weeks old C57BL/6N mice for inducing heart hypertrophy which develops into heart failure, as previously described (Lehmann L H, Rostosky J S, Buss S J, Kreusser M M, Krebs J, Mier W, Enseleit F, Spiger K, Hardt S E, Wieland T, Haass M, Lüscher T F, Schneider M D, Parlato R, Gröne H J, Haberkorn U, Yanagisawa M, Katus H A, Backs J (2014) Essential role of sympathetic endothelin A receptors for adverse cardiac remodeling. Proceedings of the National Academy of Sciences 111: 13499-13504). The substrain choice was made due to the findings published by Garcia-Menderez et al. (Garcia-Menendez L, Karamanlidis G, Kolwicz S, Tian R (2013) Substrain specific response to cardiac pressure overload in C57BL/6 mice. Am J Physiol Heart Circ Physiol 305: H397-H402) who showed that C57BL/6N mice are a better animal model for TAC-induced cardiac hypertrophy than other commonly used substrains, such as C57BL/6J. A 27-gauge needle was used for inducing the stenosis. Successful ligation was confirmed by measuring the right carotid/left carotid flow velocity ratio. Changes in heart function were determined every 2 weeks by echocardiography in non-anesthetized mice using the VisualSonics Vevo 2100 imaging system and the 55 MHz MS-550D micro scan transducer. The measurements were performed by an experimenter blinded to the treatment. Long axis and M-mode short axis cine loops were recorded. EF (ejection fraction), FS (fractional shortening) and left ventricular mass were determined using the VisualSonics software. The mice were sacrificed by $CO_2$ asphyxiation 6 weeks after surgery. Heart weight/tibia length ratio was measured as a marker of cardiac hypertrophy as well as lung weight/tibia length ratio for monitoring heart failure induced lung edema. Furthermore, body weight was tracked as well every week.

Statistical Data Analysis

The statistical data evaluation was made using GraphPad InStat 3.06 software. Differences between 3 or more different groups were assessed using One-way ANOVA followed by a Tukey's multiple comparison test for particular pairs of groups. Mann-Whitney U test was used to compare two groups. A p value <0.05 was considered significant. The mean fluorescence intensity of at least 20 images/group was analyzed in the immunohistochemistry experiments using ImageJ (FiJi version 1.51p). Western blot data were evaluated as well using ImageJ. Data are presented as mean±SD of n individual experiments. Graphs were generated using GraphPad Prism 7 (San Diego, Calif., USA).

NON-STANDARD LITERATURE CITED

Bourajjaj M, Armand A S, da Costa Martins P A, Weijts B, van der Nagel R, Heeneman S, Wehrens X H, De Windt L J (2008) NFATc2 is a necessary mediator of calcineurin-dependent cardiac hypertrophy and heart failure. Journal of Biological Chemistry 283:22295-22303

Flanagan W M, Corthesy B, Bram R J, Crabtree G R (1991) Nuclear association of a T-cell transcription factor blocked by FK-506 and cyclosporine A. Nature 352:803-807

Garcia-Menendez L, Karamanlidis G, Kolwicz S, Tian R (2013) Substrain specific response to cardiac pressure overload in C57BL/6 mice. Am J Physiol Heart Circ Physiol 305: H397-H402

Goldberg L R. In the clinic. Heart failure. Ann Intern Med. 2010 Jun. 1; 152(11):ITC61-15

Hannan R, Jenkins A, Jenkins A, Brandenburger Y (2003) Cardiac hypertrophy: A matter of translation. Clinical and Experimental Pharmacology and Physiology 30: 517-527

Hecker M, Wagner S, Henning S W, Wagner A H. Decoy oligodeoxynucleotides to treat inflammatory diseases. (book chapter) In: Therapeutic Oligonucleotides 2008; (ed. Kurreck J) RSC Publishing, Cambridge, U.K., pp. 163-188

Inagaki K, Fuess S, Storm T A, Gibson G A, Mctiernan C F, Kay M A, Nakai H (2006) Robust systemic transduction with AAV9 vectors in mice: Efficient global cardiac gene transfer superior to that of AAV8. Mol Ther 14: 45-53)

Kuriyama M, Matsushita M, Tateishi A, Moriwaki A, Tomizawa K, Ishino K, Sano S, Matsui H (2006) A cell-permeable NFAT inhibitor peptide prevents pressure-overload cardiac hypertrophy. Chemical Biology and Drug Design 67:238-243

Laupacis A, Keown P A, Ulan R A, McKenzie N, Stiller C R (1982) Cyclosporin A: a powerful immunosuppressant. Canadian Medical Association Journal 126: 1041-1046

Lehmann L H, Rostosky J S, Buss S J, Kreusser M M, Krebs J, Mier W, Enseleit F, Spiger K, Hardt S E, Wieland T, Haass M, Lüscher T F, Schneider M D, Parlato R, Gröne H J, Haberkorn U, Yanagisawa M, Katus H A, Backs J (2014) Essential role of sympathetic endothelin A receptors for adverse cardiac remodeling. Proceedings of the National Academy of Sciences 111: 13499-13504

Mak M C, Lam K M, Chan P K, Lau Y B, Tang W H, Yeung P K K, Ko B C B, Chung S M S, Chung S K (2011) Embryonic lethality in mice lacking the nuclear factor of activated T cells 5 protein due to impaired cardiac development and function. PLOS One 6: 1-8

Molkentin J D, Lu J R, Antos C L, Markham B, Richardson J, Robbins J, Grant S R, Olson E N (1998). A calcineurin-dependent transcriptional pathway for cardiac hypertrophy. Cell 93:215-228

Parra V, Rothermel B A (2017) Calcineurin signaling in the heart: The importance of time and place. J Mol Cell Cardiol 103:121-136

Pfaff M W (2001) A new mathematical model for relative quantification in real-time RT PCR. Nucleic Acids Res 29: 2003-2007

Wei S, Guo A, Chen B, Kutschke W, Xie Y P, Zimmerman K, Weiss R M, Anderson M E, Cheng H, Song L S (2010) T-tubule remodeling during transition from hypertrophy to heart failure. Novelty and significance. Circulation Research 107:520-531

Wile B M, Ban K, Yoon Y S, Bao G (2014) Molecular beacon-enabled purification of living cells by targeting cell type-specific mRNAs. Nature Protocols 9: 2411-2424

Wilkins B J, Dai Y S, Bueno O F, Parsons S A, Xu J, Plank D M, Jones F, Kimball T R, Molkentin J D (2004) Calcineurin/NFAT coupling participates in pathological, but not physiological cardiac hypertrophy. Circulation Research 94:110-118

The invention claimed is:

1. A polynucleotide comprising a Nuclear factor of activated T-cells (NFAT) binding site sequence and a reverse complement of said NFAT binding site sequence separated by a spacer sequence, wherein said polynucleotide is an RNA, wherein said NFAT binding site sequence comprises the sequence GGAAA, and wherein said polynucleotide comprises the sequence: GAGTGGAAACATACAGCCACTGAAACAGTGGCTGTATGTTTCCACTC (SEQ ID NO: 1) or a sequence at least 75% identical thereto.

2. The polynucleotide of claim 1, wherein said NFAT binding site sequence comprises the sequence RWGGAAANA, wherein R is A or G and W is A or T.

3. The polynucleotide of claim 1, wherein said polynucleotide comprises at least one further transcription factor binding site sequence and a corresponding reverse complement of said at least one further transcription factor binding site sequence.

4. The polynucleotide of claim 1, wherein said polynucleotide is a short-hairpin RNA.

5. The polynucleotide of claim 1, wherein said NFAT is NFATc1 (NFAT2, GenBank BC112243.1), NFATc2 (NFAT1, GenBank BC144074.1), NFATc3 (NFAT4, GenBank BC001050.2), and/or NFATc4 (NFAT3, GenBank BC053855.1).

6. The polynucleotide of claim 1, wherein said NFAT binding site sequence comprises the sequence NRWGGAAANA, wherein N is any base, R is A or G and W is A or T.

7. The polynucleotide of claim 1, wherein said NFAT binding site sequence comprises the sequence AGTGGAAACA.

8. A composition comprising a polynucleotide according to claim 1 and a carrier.

9. The composition of claim 8, wherein the composition is a pharmaceutical composition and wherein said carrier is a pharmaceutically acceptable carrier.

10. A method for treating and/or preventing NFAT-mediated disease in a subject suffering therefrom or expected to suffer therefrom, the method comprising:
   a) administering an effective dose of the polynucleotide according to claim 1 to said subject; and, thereby,
   b) treating and/or preventing NFAT-mediated disease.

11. The method of claim 10, wherein said administering comprises topical and/or systemic administration of said polynucleotide.

12. The method of claim 10, wherein said administering comprises epicutaeous, transcutaenous, intraarterial, or intravenous administration of said polynucleotide.

13. The method of claim 10, wherein said administering comprises catheter-assisted intraarterial or intravenous administration of said polynucleotide.

14. The method of claim 10, wherein said NFAT-mediated disease is selected from cardiac remodeling, in particular cardiomyopathy and/or heart failure; chronic inflammatory disease; and transplant rejection.

15. The method of claim 14, wherein said cardiac remodeling is caused by (i) arterial hypertension; (ii) congenital, age-related degenerative, or infection-related semilunar valve stenosis, in particular aortic valve stenosis; (iii) cardiomyopathy, in particular dilated cardiomyopathy, hypertrophic cardiomyopathy, arrhythmogenic right ventricular cardiomyopathy, left ventricular noncompaction, or restrictive cardiomyopathy; (iv) coronary heart disease; or (v) myocarditis.

* * * * *

SEQUENCE LISTING

```
<160> NUMBER OF SEQ ID NOS: 20

<210> SEQ ID NO 1
<211> LENGTH: 47
<212> TYPE: DNA
<213> ORGANISM: Artificial
<220> FEATURE:
<223> OTHER INFORMATION: NFAT stem-loop

<400> SEQUENCE: 1
gagtggaaac atacagccac tgaaacagtg gctgtatgtt tccactc          47

<210> SEQ ID NO 2
<211> LENGTH: 10
<212> TYPE: DNA
<213> ORGANISM: Artificial
<220> FEATURE:
<223> OTHER INFORMATION: NFAT 10mer binding site degenerated
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (3)..(3)
<223> OTHER INFORMATION: w is a, t, or u
<220> FEATURE:
<221> NAME/KEY: misc_feature
<222> LOCATION: (9)..(9)
<223> OTHER INFORMATION: n is a, c, g, t or u

<400> SEQUENCE: 2 nrwggaaana                                                    10

<210> SEQ ID NO 3
<211> LENGTH: 10
<212> TYPE: DNA
<213> ORGANISM: Artificial
<220> FEATURE:
<223> OTHER INFORMATION: NFAT 10mer binding site

<400> SEQUENCE: 3
agtggaaaca                                                    10

<210> SEQ ID NO 4
<211> LENGTH: 22
<212> TYPE: DNA
<213> ORGANISM: Artificial
<220> FEATURE:
<223> OTHER INFORMATION: NFAT 22mer binding site

<400> SEQUENCE: 4
gagtggaaac atacagccac tg                                      22

<210> SEQ ID NO 5
```

```
<211> LENGTH: 19
<212> TYPE: DNA
<213> ORGANISM: Artificial
<220> FEATURE:
<223> OTHER INFORMATION: NFAT binding sequence 1

<400> SEQUENCE: 5
agtggaaaga ctttccact                                              19

<210> SEQ ID NO 6
<211> LENGTH: 20
<212> TYPE: DNA
<213> ORGANISM: Artificial
<220> FEATURE:
<223> OTHER INFORMATION: NFAT binding sequence 2

<400> SEQUENCE: 6
agtggaaaca tgtttccact                                             20

<210> SEQ ID NO 7
<211> LENGTH: 20
<212> TYPE: DNA
<213> ORGANISM: Artificial
<220> FEATURE:
<223> OTHER INFORMATION: NFAT binding sequence 3

<400> SEQUENCE: 7
agtggaaaca tacagccact                                             20

<210> SEQ ID NO 8
<211> LENGTH: 18
<212> TYPE: DNA
<213> ORGANISM: Artificial
<220> FEATURE:
<223> OTHER INFORMATION: NFAT binding sequence 4

<400> SEQUENCE: 8
agtggaaacc aaaggtga                                               18

<210> SEQ ID NO 9
<211> LENGTH: 20
<212> TYPE: DNA
<213> ORGANISM: Artificial
<220> FEATURE:
<223> OTHER INFORMATION: NFAT binding sequence 5

<400> SEQUENCE: 9
agtggaaaca acaaaggtga                                             20

<210> SEQ ID NO 10
<211> LENGTH: 23
<212> TYPE: DNA
<213> ORGANISM: Artificial
<220> FEATURE:
<223> OTHER INFORMATION: NFAT binding sequence 6

<400> SEQUENCE: 10
cagagaggaa aaactgtttc ata                                         23

<210> SEQ ID NO 11
<211> LENGTH: 19
<212> TYPE: DNA
<213> ORGANISM: Artificial
<220> FEATURE:
<223> OTHER INFORMATION: NFAT binding sequence 7

<400> SEQUENCE: 11
```

```
ccaaagagga aaaattgtt                                                   19

<210> SEQ ID NO 12
<211> LENGTH: 21
<212> TYPE: DNA
<213> ORGANISM: Artificial
<220> FEATURE:
<223> OTHER INFORMATION: NFAT binding sequence 8

<400> SEQUENCE: 12
ccagtggaaa gactgtttca t                                                21

<210> SEQ ID NO 13
<211> LENGTH: 27
<212> TYPE: DNA
<213> ORGANISM: Artificial
<220> FEATURE:
<223> OTHER INFORMATION: NFAT binding site TransAM

<400> SEQUENCE: 13
cgcccaaaga ggaaaatttg tttcata                                          27

<210> SEQ ID NO 14
<211> LENGTH: 27
<212> TYPE: DNA
<213> ORGANISM: Artificial
<220> FEATURE:
<223> OTHER INFORMATION: NFAT binding sequence 9

<400> SEQUENCE: 14
cgcccaaaga ggaaaatttg tttcata                                          27

<210> SEQ ID NO 15
<211> LENGTH: 19
<212> TYPE: DNA
<213> ORGANISM: Artificial
<220> FEATURE:
<223> OTHER INFORMATION: NFAT binding sequence 10

<400> SEQUENCE: 15
ggaggaaaaa ctgtttcat                                                   19

<210> SEQ ID NO 16
<211> LENGTH: 11
<212> TYPE: DNA
<213> ORGANISM: Artificial
<220> FEATURE:
<223> OTHER INFORMATION: NFAT consensus sequence 2
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (10)..(11)
<223> OTHER INFORMATION: n is a, c, g, t or u

<400> SEQUENCE: 16
nanwggaaan n                                                           11

<210> SEQ ID NO 17
<211> LENGTH: 18
<212> TYPE: DNA
```

```
<213> ORGANISM: Artificial
<220> FEATURE:
<223> OTHER INFORMATION: NFAT consensus sequence 3
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: misc_feature
<222> LOCATION: (16)..(16)
<223> OTHER INFORMATION: n is a, c, g, t or u

<400> SEQUENCE: 17
mrtggaaama wwmnknsy                                                    18

<210> SEQ ID NO 18
<211> LENGTH: 179
<212> TYPE: DNA
<213> ORGANISM: Artificial
<220> FEATURE:
<223> OTHER INFORMATION: NFAT binding stem-loop

<400> SEQUENCE: 18
aggcgccctg caatatttgc atgtcgctat gtgttctggg aaatcaccat aaacgtgaaa      60
tgtctttgga tttgggaatc ttataagttc tgtatgagac cacagtcgac gagtggaaac    120
atacagccac tgaaacagtg gctgtatgtt tccactccac cgcagtttcg acctcgaga    179

<210> SEQ ID NO 19
<211> LENGTH: 179
<212> TYPE: DNA
<213> ORGANISM: Artificial
<220> FEATURE:
<223> OTHER INFORMATION: mutated stem-loop

<400> SEQUENCE: 19
aggcgccctg caatatttgc atgtcgctat gtgttctggg aaatcaccat aaacgtgaaa      60
tgtctttgga tttgggaatc ttataagttc tgtatgagac cacagtcgac gagcttaaac    120
atacagccac tgaaacagtg gctgtatgtt tccactccac cgcagtttcg acctcgaga    179

<210> SEQ ID NO 20
<211> LENGTH: 11
<212> TYPE: DNA
<213> ORGANISM: Artificial
<220> FEATURE:
<223> OTHER INFORMATION: stem-loop of Fig. 7

<400> SEQUENCE: 20
atgcaaagca t                                                           11
```